US011850331B2

(12) United States Patent
Gupta et al.

(10) Patent No.: US 11,850,331 B2
(45) Date of Patent: Dec. 26, 2023

(54) DEVICES WITH ANTI-THROMBOGENIC AND ANTI-MICROBIAL TREATMENT

(71) Applicant: TELEFLEX MEDICAL INCORPORATED, Morrisville, NC (US)

(72) Inventors: Nisha Gupta, Audubon, PA (US); Chuanting You, Sinking Spring, PA (US); Kamna Giare-Patel, Wyomissing, PA (US); Kevin Sechrist, Womelsdorf, PA (US)

(73) Assignee: Teleflex Medical Incorporated, Morrisville, NC (US)

( * ) Notice: Subject to any disclaimer, the term of this patent is extended or adjusted under 35 U.S.C. 154(b) by 0 days.

(21) Appl. No.: 14/774,602

(22) PCT Filed: Mar. 10, 2014

(86) PCT No.: PCT/US2014/022574
§ 371 (c)(1),
(2) Date: Sep. 10, 2015

(87) PCT Pub. No.: WO2014/164487
PCT Pub. Date: Oct. 9, 2014

(65) Prior Publication Data
US 2016/0015863 A1 Jan. 21, 2016

Related U.S. Application Data

(60) Provisional application No. 61/879,623, filed on Sep. 18, 2013, provisional application No. 61/776,104, filed on Mar. 11, 2013.

(51) Int. Cl.
A61L 29/08 (2006.01)
C09D 175/04 (2006.01)
A61L 29/16 (2006.01)
D01D 5/24 (2006.01)
A61M 25/00 (2006.01)

(52) U.S. Cl.
CPC ............ A61L 29/085 (2013.01); A61L 29/16 (2013.01); C09D 175/04 (2013.01); D01D 5/24 (2013.01); A61L 2300/206 (2013.01); A61L 2300/404 (2013.01); A61L 2300/42 (2013.01); A61M 2025/0056 (2013.01)

(58) Field of Classification Search
CPC ..... A61L 29/085; A61L 29/16; C09D 175/04; D01D 5/24
See application file for complete search history.

(56) References Cited

U.S. PATENT DOCUMENTS

| | | |
|---|---|---|
| 4,592,341 A | 6/1986 | Omagari et al. |
| 4,601,713 A | 7/1986 | Fuqua |
| 4,671,291 A | 6/1987 | Wilson |
| 4,722,344 A | 2/1988 | Cambron et al. |
| 4,734,097 A | 3/1988 | Tanabe et al. |
| 4,781,677 A | 11/1988 | Wilcox |
| 4,807,626 A | 2/1989 | McGirr |
| 4,832,023 A | 5/1989 | Murphy-Chutorian et al. |
| 4,893,621 A | 1/1990 | Heyman |
| 4,898,591 A | 2/1990 | Jang et al. |
| 4,917,667 A | 4/1990 | Jackson |
| 4,925,668 A | 5/1990 | Khan et al. |
| 4,955,377 A | 9/1990 | Lennox et al. |
| 5,026,377 A | 6/1991 | Burton et al. |
| 5,059,177 A | 10/1991 | Towne et al. |
| 5,084,054 A | 1/1992 | Bencini et al. |
| 5,091,205 A | 2/1992 | Fan |
| 5,102,401 A | 4/1992 | Lambert et al. |
| 5,108,366 A | 4/1992 | Schatz |
| 5,108,416 A | 4/1992 | Ryan et al. |
| 5,147,370 A | 9/1992 | McNamara et al. |
| 5,154,725 A | 10/1992 | Leopold |
| 5,165,952 A | 11/1992 | Solomon et al. |
| 5,167,239 A | 12/1992 | Cohen et al. |
| 5,167,623 A | 12/1992 | Cianci et al. |
| 5,201,732 A | 4/1993 | Parins et al. |
| 5,241,970 A | 9/1993 | Johlin et al. |
| 5,242,428 A | 9/1993 | Palestrant |

(Continued)

FOREIGN PATENT DOCUMENTS

| | | |
|---|---|---|
| CN | 101426539 A | 5/2009 |
| EP | 3332817 A1 | 6/2018 |

(Continued)

OTHER PUBLICATIONS

Feeley, Domiic, Multi-layer Extrustion Processes Tackle Tubing Challenges, May 16, 2012, pp. 1-8 (Year: 2012).*
Dictionary.com, Solute, acessed Jan. 10, 2022, pp. 1-5. (Year: 2022).*
M. Ryder et al., "The Effect of Chlorhexidine Catheter Coating Compared to an Uncoated and Biomimetic Catheter on the Reduction of Fibrin Sheath Formation in an in vivo Clinically Simulated Ovine Model", SHEA (Conference Proceeding), Jacksonville, FL, Apr. 2012, 1 page.
Krein et al., Mayo Clin. Proc., vol. 82, 2007, pp. 672-678.
Hemmelgarn et al., New Engl. J. Med., vol. 364, 2011, pp. 303-312.

(Continued)

Primary Examiner — Andrew S Rosenthal
Assistant Examiner — Lyndsey M Beckhardt
(74) Attorney, Agent, or Firm — BakerHostetler

(57) ABSTRACT

A medical device adapted for contact with a vessel or cavity in the body including a tubular portion is provided. The device has an external surface including an external substance that is at least one of a coating or an impregnation, comprising alexidine in an amount that is both anti thrombogenically effective and anti microbially effective. The device also has an internal surface including an internal substance that is at least one of a coating or an impregnation, comprising alexidine in an amount that is both anti thrombogenically effective and anti microbially effective.

23 Claims, 21 Drawing Sheets

(56) References Cited

U.S. PATENT DOCUMENTS

| | | | |
|---|---|---|---|
| 5,273,527 | A | 12/1993 | Schatz et al. |
| 5,292,305 | A | 3/1994 | Boudewijn et al. |
| 5,328,698 | A * | 7/1994 | Onwumere ............. A61L 27/54 424/426 |
| 5,334,143 | A | 8/1994 | Carroll |
| 5,707,366 | A | 1/1998 | Solomon et al. |
| 5,897,911 | A * | 4/1999 | Loeffler ................. A61F 2/82 427/2.25 |
| 5,902,283 | A | 5/1999 | Darouiche et al. |
| 6,039,755 | A | 3/2000 | Edwin et al. |
| 6,313,254 | B1 | 11/2001 | Meijs et al. |
| 6,517,548 | B2 | 2/2003 | Lorentzen Cornelius et al. |
| 6,565,591 | B2 | 5/2003 | Brady et al. |
| 6,627,724 | B2 | 9/2003 | Meijs et al. |
| 7,029,467 | B2 | 4/2006 | Currier et al. |
| 7,641,645 | B2 | 1/2010 | Schur |
| 7,803,395 | B2 | 9/2010 | Datta et al. |
| 7,879,444 | B2 | 2/2011 | Jiang et al. |
| 7,892,469 | B2 | 2/2011 | Lim et al. |
| 8,008,407 | B2 | 8/2011 | Oberhellman et al. |
| 8,017,686 | B2 | 9/2011 | Buter et al. |
| 8,084,535 | B2 | 12/2011 | Maton et al. |
| 8,308,699 | B2 | 11/2012 | Zhang et al. |
| 2001/0010016 | A1 | 7/2001 | Modak et al. |
| 2003/0049300 | A1* | 3/2003 | Terry ..................... A61L 27/34 424/423 |
| 2004/0208985 | A1* | 10/2004 | Rowan .................. A61L 27/34 427/2.25 |
| 2007/0154621 | A1 | 7/2007 | Raad |
| 2009/0029961 | A1 | 1/2009 | Modak et al. |
| 2009/0118455 | A1 | 5/2009 | Gunatillake et al. |
| 2009/0155335 | A1 | 6/2009 | O'Shaughnessey et al. |
| 2009/0156460 | A1 | 6/2009 | Jiang et al. |
| 2009/0259015 | A1 | 10/2009 | Jiang et al. |
| 2010/0082097 | A1 | 4/2010 | Rosenblatt et al. |
| 2010/0145286 | A1 | 6/2010 | Zhang et al. |
| 2010/0152708 | A1 | 6/2010 | Li et al. |
| 2010/0135949 | A1 | 7/2010 | Ou-Yang |
| 2010/0196434 | A1* | 8/2010 | Gupta .................... A61L 29/16 424/423 |
| 2011/0054581 | A1 | 3/2011 | Desai et al. |
| 2011/0097277 | A1 | 4/2011 | Jiang et al. |
| 2011/0150961 | A1* | 6/2011 | Perry ..................... A61K 31/74 424/411 |
| 2011/0282005 | A1 | 11/2011 | Jiang et al. |

FOREIGN PATENT DOCUMENTS

| | | |
|---|---|---|
| JP | 4226670 B2 | 12/2008 |
| JP | 2011-156589 A | 8/2011 |
| JP | 2012-510339 A | 5/2012 |
| JP | 2012-510559 A | 5/2012 |
| WO | 98/08884 A1 | 3/1998 |
| WO | 1998013405 A1 | 4/1998 |
| WO | 2000064971 A1 | 11/2000 |
| WO | 2011/156589 A1 | 12/2011 |
| WO | 2013033159 A1 | 3/2013 |

OTHER PUBLICATIONS

Trautner et al., Arch. Intern. Med., vol. 164, 2004, pp. 842-850.
O'Grady et al., Pediatrics, vol. 110, 2002, pp. e51-e75.
Chen et al., J. Periodontol., vol. 74, No. 11, 2003, pp. 1652-1659.
Milstone et al., Healthcare Epidemiology, vol. 46, 2008, pp. 274-281.
Thomson et al., Clinical Nephrology, vol. 75, No. 3, 2011, pp. 212-217.
Pierce et al., Pharmacotherapy, vol. 30, 2010, pp. 1150-1158.
Willms; Vercaigne, Semin. Dial., vol. 21, 2008, pp. 71-77.
Mandolfo et al., J. Vasc. Access., vol. 7, 2006, pp. 99-102.
Nakonechna et al., Allergol. Immunopathol. (Madr.), vol. 42, No. 1, 2012, pp. 44-49.
Noel et al., Ann. R. Col.. Surg. Engl., vol. 94, 2012, pp. e159-e160.
Aber et al., Acta Anaesthesiol. Belg., vol. 63, 2012, pp. 191-194.
Guleri et al., Surg. Infect. (Larchmt)., vol. 13, 2012, pp. 171-174.
Khoo; Oziemski, Heart Lung Circ., vol. 20, 2011, pp. 669-670.
Jee et al., Br. J. Anaesth., vol. 103, 2009, pp. 614-615.
Pham et al., Clin Exp Allergy., vol. 30, 2000, pp. 1001-1007.
Roberts et al., J. Clin Periodontol., vol. 8, 1981, pp. 213-219.
Ganendren et al., Antimicrob. Agents Chemother., vol. 48, 2004, pp. 1561-1569.
Chawner et al., J Appl Bacteriol., vol. 66, 1989, pp. 253-258.
Zorko et al., J. Antimicrob. Chemother. 2008, vol. 62, 2008, pp. 730-737.
Grissino-Mayer, Tree-Ring Research., vol. 59, 2003, pp. 63-79.
Huynh et al., Eur. J. Pharm. Biopharm., vol. 74, 2010, pp. 255-264.
Tew et al., Acc. Chem. Res., vol. 43, No. 1, 2010, pp. 30-39.
Gao et al., Int. J. Clin. Exp. Med., vol. 6, 2013, pp. 259-268.
Kallmes et al., Am. J. Neuroradiol., vol. 18, 1997, pp. 1243-1251.
Wilner et al., Circulation Res., vol. 43, 1978, pp. 424-428.
Wang "Thesis", 1998, Polytechnic Institute and State Univ., article "Polydimethylsiloxane Modification of Segmented Thermoplastic Polyurethanes and Polyureas".
Lok et al., Nephrol. Dial. Transplant., vol. 22, 2007, pp. 477-483.
Ahn et al., Anesth. Analg., vol. 95, 2002, pp. 1125.
Iserson "J .-F.-B. Charriere: the man behind the "French" gauge", J. Emerg. Med., vol. 5, 1987, pp. 545-548, XP023254850.
Qiu; Park, Adv. Drug Delivery Reviews., vol. 53, 2001, pp. 321-339.
Bromberg; Ron, Adv. Drug Delivery Reviews, vol. 31, 1998, pp. 197-221.
Wei et al., Biomaterials, vol. 30, 2009, pp. 2606-2613.
Westhaus; Messersmith, Biomaterials, vol. 22, 2001, pp. 453-462.
Sosnik; Cohn, Biomaterials, vol. 25, 2004, pp. 2851-2858.
Kim et al., Biomacromolecules, vol. 10, 2009, pp. 2476-2481.
Mort, Critical Care and Trauma., vol. 105, 2007, pp. 1357-1362.
Taylor et al., Radiology, vol. 229, 2003, pp. 99-108.
Akahoshi et al., Brit. J. Radiology, vol. 74, 2001, pp. 1017-1022.
Walter et al., J. Spinal Cord Med., vol. 32, 2009, pp. 578-582.
Mohammed et al., Expert Rev. Med. Devices., vol. 5, 2008, pp. 705-707.
Durst et al., Imaging and Diagnostic Methods, vol. 9, 2007, pp. 290-293.
AARC Clinical Practice Guidelines, Respir. Care., vol. 55, 2010, pp. 758-764.
Thomas et al., J. Invasive Cardiol., vol. 23, 2011, pp. 536-539.
Besarab et al., Clin. J. Am. Soc. Nephrol., vol. 6, 2011, pp. 227-234.
Knuttinen et al., Seminars in Interventional Radiology, vol. 26, 2009, pp. 106-114.
Royle et al., Ann. R. Coll. Surg. Engl., vol. 90, 2008, pp. 679-684.
Fong et al., Acta. Biomater., vol. 6, 2010, pp. 2554-2556.
Brazel and Rosen (2012) Fundamental Principles of Polymeric Materials, 3rd ed., Wiley, New York, NY.
Jespersen et al., Acta Haematol, vol. 67, 1982, pp. 2-7.
Slizova, D; Otakar, K; Pospisilova, B.: "Alternative Method of Rapid Drying Vascular Specimans for Scanning Electron Microscopy", Journal of Endovascular Therapy, vol. 10, 2003, pp. 285-187.
Berra et al., Intensive Care Med., vol. 34, 2008, pp. 1020-1029.
Osman et al., Scand. J. Clin. Lab. Invest., vol. 69, 2009, pp. 395-400.
Aslam; Darouiche, Infect. Control Hosp. Epidemiol., vol. 31, 2010, pp. 1124-1129.
Hachem et al., Antimicrobial Agents Chemotherapy, vol. 53, 2009, pp. 5145-5149.
Bakke et al., J. Microbiol.. Methods., vol. 44, 2001, pp. 13-26.
Saljoughian; Williams, Curr. Pharm. Des., vol. 6, 2000, pp. 1029-1056.
Ashby et al., "Engineering Materials 1", 2012, Elsevier, pp. 115-133.
Schick et al., Critical Care, vol. 13, No. R191, 2009, 15 pages.
Venkatesh et al., J. Medical Microbiol., vol. 58, 2009, pp. 936-944.
Peeters et al., J. Microbiol. Methods., vol. 72, 2008, pp. 157-165.

(56) References Cited

OTHER PUBLICATIONS

Vijayanand, et al., "Interpreting Blood-Biomaterial Interactions from Surface Free Energy and Work of Adhesion", Trends in Biomaterials and Artificial Organs, vol. 18, 2005, pp. 73-83.
Howell et al., "Endoscopic needle aspiration biopsy at ERCP in the diagnosis of biliary strictures," Gastrointestinal Endoscopy, vol. 38, Issue 5, 1992, pp. 531-535.
Waye J.D. et al., "Suction Retrieval of the Small Colon Polyp," Spring, vol. 10, Issue 4, 1998, pp. 199-201.

\* cited by examiner

DEVICES WITH ANTI-THROMBOGENIC AND ANTI-MICROBIAL TREATMENT

CROSS REFERENCE

This application is a National Stage of International Application No. PCT/US2014/022574, filed on Mar. 10, 2014, which claims the benefit of priority of U.S. Ser. No. 61/776,104, filed Mar. 11, 2013, entitled "Novel Enhanced Devices with AntiThrombogenic Coating," which is hereby incorporated by reference in its entirety, and claims the benefit of priority of U.S. Ser. No. 61/879,623, filed Sep. 18, 2013, entitled "Novel Enhanced Devices with Anti-Thrombogenic and Anti-Microbial Coating," which is also incorporated herein by reference in its entirety.

FIELD OF THE DISCLOSURE

The present disclosure relates to formulations for treating medical devices, the combination of a medical device in contact with a solution, methods for treating, coating, or impregnated a medical device, a medical device that is treated, coated, or impregnated, and methods for clinical use of the medical device.

BACKGROUND OF THE DISCLOSURE

Catheters and other devices that are implanted into vessels or cavities in the clinical or veterinary situation are associated with infections, such as local infections and blood-stream infections, as well as infections that comprise a biofilm. Catheter-related bloodstream infections affect over 2 million hospitalized patients per year (Krein et al (2007) Mayo Clin. Proc. 82:672-678). Catheters may be accessed multiple times per day, for example, for taking measurements or obtaining samples for laboratory analysis. Multiple samplings increase the potential for contamination and infections. Short-term catheters are more associated with microbial contamination of the external surface of the catheter, while microbial colonization at the internal surface as well as intraluminal colonization are associated with long-term implantation. About half of hemodialysis catheters fail within 1 year. Up to two thirds of the failures are due to thrombosis. Infection related to central venous catheters, and catheter-related sepsis is one of the most common causes of death in patients undergoing hemodialysis (Hemmelgarn et al (2011) New Engl. J. Med. 364:303-312).

Catheters, catheter cuffs, and other catheter components, are sometimes treated, coated, or impregnated (or any combination thereof) with antimicrobial or antiseptic agents, with the goal of decreasing infections.

Use of catheters impregnated with agents, such as chlorhexidine, can partially reduce the risk of infections (see, e.g., Trautner and Darouiche (2004) Arch. Intern. Med. 164:842-850). Chlorhexidine has been used for coating medical devices, including catheters, cuffs, and synthetic membranes (see, e.g., O'Grady et al (2002) Pediatrics 110: e51-e75; Chen, et al (2003) J. Periodontol. 74:1652-1659). This agent has broad activity against gram positive and negative bacteria, as well as against yeasts and some viruses (Milstone, et al. (2008) Healthcare Epidemiology 46:274-281). In addition to the problem of infections and biofilms, indwelling catheters can result in the problem of pathological blood clot formation, that is, in catheter-induced thrombosis (Thomson et al (2011) Clin. Nephrol. 75:212-217; Pierce and Rocco (2010) Pharmacotherapy. 30:1150-1158; Willms and Vercaigne (2008) Semin. Dial. 21:71-77; Mandolfo et al (2006) J. Vasc. Access. 7:99-102). In an attempt to overcome the problem of catheter-induced clot formation, patients have been treated with warfarin. Also, anti-coagulants such as heparin or citrate have been used as locking solutions for the catheter. Unfortunately, the approaches of warfarin treatment, or using locking solutions that include heparin or citrate, result in significant safety issues in patients. Hence, the present disclosure addresses the unmet need for an indwelling catheter, or other medical device, with a reduced tendency to lead to infections and pathological blood clotting, while maintaining an acceptable safety profile.

Exposure to chlorhexidine, including exposure to chlorhexidine from chlorhexidine-treated catheters, can result in allergic reactions, including life-threatening anaphylaxis, as documented by Nakonechna et al (2012) Allergol. Immunopathol. (Madr.) S0301-0546(12)00262-5; Noel et al (2012) Ann. R. Col. Surg. Engl. 94:e159-e160; Faber et al (2012) Acta Anaesthesiol. Belg. 63:191-194; Guleri et al (2012) Surg. Infect. (Larchmt). 13:171-174, Khoo and Oziemski (2011) Heart Lung Circ. 20:669-670; Jee et al (2009) Br. J. Anaesth. 103:614-615; and Pham et al (2000) Clin Exp Allergy. 30:1001-1007.

Alexidine and chlorhexidine have been described and compared (see, e.g., Roberts et al (1981) J. Clin Periodontol. 8:213-219; Ganendren et al (2004) Antimicrob. Agents Chemother. 48:1561-1569; Chawner et al (1989) J Appl Bacteriol. 66:253-258; Zorko et al (2008) J. Antimicrob. Chemother. 2008; 62:730-737).

The present disclosure addresses the unmet need for a medical device treated with a broad-spectrum antimicrobial agent with reduced potential for allergic reactions. This unmet need is addressed with alexidine, a broad-spectrum antimicrobial agent that is effective at lower concentrations and different, in terms of chemical structure, than with chlorhexidine, and thus has less potential for inducing an allergic reaction. The over-utilization of chlorhexidine has resulted in an increased prevalence of allergic reactions to chlorhexidine. Moreover, because alexidine is antigenically different from chlorhexidine, alexidine has reduced potential for boosting any existing anti-chlorhexidine immune response in any given patient.

Due to the easy availability of a major raw material 4-chloro-aniline (PCA) from the petrochemical industry, as well as promotion by Imperial Chemical Industries as a disinfectant and topical antiseptic in the United Kingdom in the 1950s, chlorhexidine has been synthesized in large quantities and at low cost, and widely used around world as an antiseptic solution. Chlorhexidine and alexidine are biguanide compounds. Alexidine is commercially available but is more expensive than chlorhexidine, due to the greater number of synthetic steps involved in alexidine synthesis. The starting material, 2-ethyl-hexyl amine, is not readily available in large quantities, resulting in a higher cost for alexidine. Another challenge of alexidine is its relatively low solubility in water, when compared to chlorhexidine gluconate (CHG). CHG is highly soluble in water, accounting for its wide used in applications such as mouth rinse, contact lens solutions, soaps, and sanitizers. Despite these challenges, the present disclosure discloses medical devices treated, coated, or impregnated (or any combination thereof) with alexidine, and provides compositions, devices, and methods, that are novel and enhanced.

SUMMARY OF THE DISCLOSURE

Briefly stated, disclosed are medical devices, including catheters, cannulas, and valves, that are treated, coated, impregnated, or bulk-distributed with an agent that is both anti-thrombogenic and anti-microbial. Also disclosed are formulations, methods of clinical use, and methods of manufacture.

The present disclosure provides a medical device adapted for contact with a vessel or cavity in the body, the medical device including a tubular portion comprising an external surface including an external substance that is at least one of a coating or an impregnation, comprising alexidine in an amount that is both anti-thrombogenically effective and anti-microbially effective; and an internal surface including an internal substance that is at least one of a coating or an impregnation, comprising alexidine in an amount that is both anti-thrombogenically effective and anti-microbially effective.

Also provided is the above medical device, wherein the external substance, comprises alexidine at a first concentration (micrograms/square centimeter; ug/cm$^2$), wherein the external substance comprises alexidine at a second concentration (ug/cm$^2$), and wherein the first concentration is not the same as the second concentration.

Further encompassed is the above medical device, wherein the external substance and the internal substance comprises a non-alexidine solute.

Additionally provided is the above medical device, wherein the external substance comprises an external substance solute group composed of all solutes present in the external substance, wherein the external substance solute group includes at least one non-alexidine solute. The medical device further comprises an internal substance solute group composed of all solutes present in the internal substance, wherein the internal substance solute group includes at least one non-alexidine solute, wherein (i) the external substance solute group is not the same as the internal substance solute group or (ii) at least one solute is at a different concentration in the external substance solute group than in the internal substance solute group. The skilled artisan will understand that, in measuring the content of solutes in a manufactured medical device, it will be the case that any measurement excludes solvents, such as acetone or methanol. Residual solvent may or may not be present at the time of determination of solute.

In another aspect, the present disclosure provides the above medical device, wherein the external substance solute group is not the same, in terms of chemical composition, as the internal substance solute group, and the medical device further comprises at least one distinguishing solute present in only one of the external substance solute group or the internal substance solute group, wherein (i) the at least one distinguishing solute comprises a polymer that is not covalently bound to the medical device, or (ii) the at least one distinguishing solute comprises an anion.

What is also embraced is the above medical device, wherein the at least one distinguishing solute comprises: (i) a polyurethane polymer that is not covalently bound to the medical device, or (ii) an ion that is acetate ion or gluconate ion.

Also encompassed, is the above medical device, wherein the external substance comprises alexidine at a first concentration (ug/cm$^2$) that is less than about 500 ug/cm$^2$. Also provided is the above medical device, wherein the external substance comprises alexidine at a first concentration (ug/cm$^2$) that is less than about 300 ug/cm$^2$. Also provided is the above medical device, wherein the external substance comprises alexidine at a first concentration (ug/cm$^2$) that is less than about 100 ug/cm$^2$.

In another aspect, what is also provided is the above medical device, wherein (i) the alexidine is capable of reducing a thrombogenic event that takes place on one or both of said external surface and internal surface, and wherein (ii) the alexidine is capable of reducing microbial activity that takes place on one or both of said external surface and internal surface.

In yet another embodiment, what is provide is the above medical device, wherein the external surface comprises alexidine at a concentration (µg/cm$^2$) that is capable of reducing thrombogenic events, and wherein said concentration is such that a comparator medical device with an external surface comprising chlorhexidine at the same said concentration is not capable of detectably reducing thrombogenic events.

Also provided is the above medical device, wherein the external surface comprises alexidine at a concentration (µg/cm$^2$) that is capable of reducing thrombogenic events down to a low range that is in the range of 0-50%, relative to an uninhibited thrombogenic event level defined as 100%, and wherein said concentration is such that a comparator medical device with an external surface comprising chlorhexidine at the same said concentration is capable of reducing thrombogenic events to a range of 90.0-99.9%, where the uninhibited thrombogenic event level is defined as 100%.

Also provided is the above medical device, wherein the internal surface comprises alexidine at a concentration (µg/cm$^2$) that is capable of reducing thrombogenic events to a relatively large extent that is in the range of 0-50%, relative to an uninhibited thrombogenic event level defined as 100%, and wherein said concentration is such that a comparator medical device with an internal surface comprising chlorhexidine at the same said concentration is capable of reducing thrombogenic events to a range of 90.0-99.9%, where the uninhibited thrombogenic event level is defined as 100%.

Additionally, what is embraced is the above medical device, wherein the medical device comprises one or more of alexidine, alexidine hydrochloride, alexidine dihydrochloride, alexidine monoacetate, alexidine diacetate, alexidine gluconate, or alexidine digluconate.

Moreover, what is provided is the above medical device, comprising an inner surface substance that comprises a first composition that includes alexidine and optionally additional solutes, and an outer surface substance that comprises a second composition that includes alexidine and optionally additional solutes, wherein the first composition has the same solutes as the second composition.

In another aspect, what is provided is the above medical device, wherein the alexidine that is comprised by the medical device is sufficient in concentration to result in a change in blood clotting time of at least 150% or at least a 50% increase in blood clotting time, when compared to the clotting time with a control medical device that does not comprise alexidine, as measured using human whole blood for measuring blood clotting time.

Also provided is the above medical device, wherein the concentration of alexidine is sufficient to result in less than 90% of maximal platelet deposition on the medical device, as compared to platelet deposition with a control medical device that does not comprise alexidine, wherein maximal platelet deposition is defined as 100%.

Also contemplated is the above medical device, wherein the alexidine content is one of: (i) at least 100 micrograms per cm$^2$ of external surface area; and (ii) at least 10 micrograms per cm$^2$ of internal surface area or (iii) at least 100 micrograms per cm² of external surface area and at least 10 micrograms per cm² of internal surface area.

In another aspect, what is provided is the above medical device wherein the alexidine content is one or both of: (i) at least 200 micrograms per cm² of external surface area; and (ii) at least 20 micrograms per cm² of internal surface area or (iii) at least 200 micrograms per cm² of external surface and at least 20 micrograms per cm² of internal surface area.

In another embodiment, what is provided is the above medical device, wherein the alexidine is bulk distributed. In an embodiment, any medical device that does not have bulk-distribution of an anti-microbial agent may be excluded. Yet in another embodiment, any medical device that has bulk-distribution of an anti-microbial agent may be excluded.

Also provided is the above medical device that comprises one or more of a catheter, cannula, elongated tube, valve, or implant port. Also, what is provided is the above medical device that is adapted for contact with or insertion into one or more of the vascular system, the urinary tract, or the respiratory system. In an exclusionary embodiment, what is provided is the above medical device that does not comprise chlorhexidine.

In polymer embodiments, what is provided is the above medical device that comprises a coating containing a polymer that comprises polyether polyurethane, polyester polyurethane, polycarbonate polyurethane, or polydimethylsiloxane polyurethane. In another polymer embodiment, what is provided is the above medical device, wherein the internal substance, the external substance, or both the internal substance and external substance, comprise a polymer that comprise polysulfobetaine, polycarboxybetaine, or both polysulfobetaine and polycarboxybetaine. In another polymer embodiment, what is provided is the above medical device, wherein the internal substance, the external substance, or both the internal and external substance, comprises a co-polymer of silicone macrodiols and polyurethanes.

In a methods of use embodiment, the present disclosure provides a method for storing a medical device in a mammalian subject, wherein the medical device resides at least partly in the blood vessel lumen, the method comprising the steps of: (i) inserting at least part of the medical device in the blood vessel lumen, followed by, (ii) administering a solution, withdrawing a biological fluid, or administering a solution and also withdrawing a biological fluid, followed by, (iii) withdrawing the medical device from the blood vessel lumen, wherein the medical device comprises a surface that is capable of contacting blood in the vascular system, wherein the medical device comprises an amount of alexidine that is both anti-thrombogenically effective and anti-microbially effective, and wherein in use the alexidine is capable of reducing thrombogenic events and is capable of reducing microbial activity.

Also provided is the above method, wherein the solution is a sterile solution, a pharmacological agent, or a diagnostic agent.

Further provided is the above method, wherein the medical device comprises an external surface, and wherein the alexidine content is at least 50 micrograms per cm² of external surface area, and wherein the alexidine that is comprised by the external surface of the medical device is sufficient to result in a change in blood clotting time of at least 125% or at least a 25% increase in blood clotting time, when compared to the blood clotting time with a control medical device that does not comprise alexidine, using human whole blood for measuring blood clotting time.

Also provided is the above method, wherein the medical device comprises an external surface, and wherein the alexidine content is less than about 200 micrograms per cm² (ug/cm²) of external surface area, and wherein the alexidine that is comprised by the external surface of the medical device is sufficient to result in a change in blood clotting time of at least 125% or at least a 25% increase in blood clotting time, when compared to the blood clotting time with a control medical device that does not comprise alexidine, using human whole blood for measuring blood clotting time.

In yet another method embodiment, what is provided is the above method, wherein medical device comprises an internal surface and an external surface, wherein the external surface includes an external substance that is defined as a coating, impregnation, or both a coating and an impregnation, wherein the external substance comprises alexidine, and wherein the internal surface includes an internal substance that is defined as a coating, impregnation, or both a coating and an impregnation, wherein the internal substance comprises alexidine, and wherein the concentration of alexidine in the external substance is greater than the concentration of alexidine in the internal substance.

In a manufacturing method embodiment, the present disclosure provides a method for manufacturing a medical device that comprises alexidine, comprising the steps of: (1) acquiring a medical device that comprises an external surface and an internal surface, (2) contacting the external surface with a first solution that comprises alexidine, and contacting the internal surface with a second solution that comprises alexidine, (3) maintaining a contact of the external surface with the first solution for a time sufficient to produce an external surface that comprises alexidine; and maintaining a contact of the internal surface with the second solution for a time sufficient to produce an internal surface that comprises alexidine, (4) drying or removing any residual solution from the medical device that comprises alexidine, wherein the medical device that comprises alexidine comprises an amount of alexidine that is both anti-thrombogenically effective and anti-microbially effective.

Also provided is the above manufacturing method, wherein the external surface is contacted with the solution for a first time frame, and the internal surface is contacted with the solution for a second time frame, wherein the first time frame at least partially overlaps the second time frame.

Also provided is the above manufacturing method, wherein the alexidine concentration of the first solution is not the same as the alexidine concentration as the second solution. Further provided is the above manufacturing method, wherein the contacting of the external surface comprises one or more of dipping, soaking, spraying, or wiping; and wherein the contacting of the internal surface comprises one or more of dipping, soaking, spraying, or wiping Also provided is the above manufacturing method, wherein the first solution comprises one or both of tetrahydrofuran and methanol, or wherein the second solution comprises one or more of tetrahydrofuran, methanol, ethanol, isopropyl alcohol, citric acid, and citric acid trisodium salt.

Also provided is the above manufacturing method, wherein: (i) the first solution comprises a soluble plastic polymer, (ii) the second solution comprises a soluble plastic polymer, (iii) the first solution comprises a soluble plastic polymer and the second solution comprises a soluble plastic polymer, or (iv) the first solution does and the second solution does not contain a soluble plastic polymer.

In a solutions embodiment, the present disclosure provides a solution configured for coating or impregnating, or for both coating and impregnating, a medical device with alexidine, the solution comprising: (i) at least 0.05% alexidine, (ii) a solvent comprising tetrahydrofuran (THF) and methanol, THF and ethanol, or THF and isopropyl alcohol, or THF and citric acid, or THF and isopropyl alcohol and citric acid. Also provided is the above solution, that further comprises a soluble polymer. Also provided is the above solution, that further comprises a soluble polymer that is soluble polyurethane.

The present disclosure provides a medical device adapted for contact with a vessel or cavity in the body, the medical device comprising a tubular portion that comprises an external surface with a coating, an impregnation, or both (the combination of both a coating an impregnation), and an internal surface with a coating, an impregnation, or both, wherein the external coating, impregnation, or both, comprises alexidine in an amount that is both anti-thrombogenically effective and anti-microbially effective, and wherein the internal coating, impregnation, or both, comprises alexidine in an amount that is both anti-thrombogenically effective and anti-microbially effective.

What is also embraced, is the above medical device, wherein external coating, impregnation, or both, comprises a first solute that is not alexidine, and the internal coating, impregnation, or both comprises a second solute that is not alexidine, and (i) wherein the first solute is not the same in terms of chemical composition as the second solute, or (ii) wherein the first solute occurs at a different concentration in the medical device than the second solute.

Also provided is the above medical device, wherein the external coating, impregnation, or both, comprises alexidine at a first concentration (micrograms/square centimeter; ug/cm$^2$), wherein the external coating, impregnation, or both, comprises alexidine at a second concentration (ug/cm$^2$), and wherein the first concentration does not have the same value (ug/cm$^2$) for alexidine as the second concentration.

Alternative units of measurements can be used, for example, micrograms per square centimeter to a depth of about 50 micrometers; micrograms per square centimeter to a depth of about 100 micrometers; micrograms per square centimeter to a depth of about one millimeter; micrograms per square centimeter to a depth of about two millimeters, and so on. Other alternative units can be used, for example, picograms per cubic millimeter, nanograms per cubic millimeter, micrograms per cubic millimeter, and so on.

In another aspect, what is provided is the above medical device, wherein the external surface comprises a first coating, impregnation, or both, and the internal surface comprises a second coating, impregnation, or both, wherein the first coating, impregnation, or both, has a solute composition that is not the same as the solute composition of the second coating, impregnation, or both.

Also provided is the above medical device, wherein the external coating, impregnation, or both, comprises alexidine at a first concentration (ug/cm$^2$) that is less than about 400 ug/cm$^2$.

Also provided is the above medical device, wherein the external coating, impregnation, or both, comprises alexidine at a first concentration (ug/cm$^2$) that is less than about 300 ug/cm$^2$.

Also provided is the above medical device, wherein the external coating, impregnation, or both, comprises alexidine at a first concentration (ug/cm$^2$) that is less than about 200 ug/cm$^2$.

Also provided is the above medical device, wherein the external coating, impregnation, or both, comprises alexidine at a first concentration (ug/cm$^2$) that is less than about 150 ug/cm$^2$.

Also provided is the above medical device, wherein the external coating, impregnation, or both comprises alexidine at a first concentration (ug/cm$^2$) that is less than about 100 ug/cm$^2$.

Also contemplated is the above medical device, wherein the external coating, impregnation, or both, comprises alexidine at a first concentration (ug/cm$^2$) that is less than about 85 ug/cm$^2$.

Also contemplated is the above medical device, wherein the external coating, impregnation, or both, comprises alexidine at a first concentration (ug/cm$^2$) that is less than about 80 ug/cm$^2$.

Moreover, what is further provides is the above medical device, wherein the external coating, impregnation, or both, comprises alexidine at a first concentration (ug/cm$^2$) that is less than about 75 ug/cm$^2$.

Moreover, what is further provides is the above medical device, wherein the external coating, impregnation, or both comprises alexidine at a first concentration (ug/cm$^2$) that is less than about 70 ug/cm$^2$.

Internal surfaces with internal coatings, impregnations, or both, which are encompassed by the present disclosure, include the following.

Also provided is the above medical device, wherein the internal coating, impregnation, or both, comprises alexidine at a first concentration (ug/cm$^2$) that is less than about 300 ug/cm$^2$.

Also provided is the above medical device, wherein the internal coating, impregnation, or both, comprises alexidine at a first concentration (ug/cm$^2$) that is less than about 200 ug/cm$^2$.

Also provided is the above medical device, wherein the internal coating, impregnation, or both comprises alexidine at a first concentration (ug/cm$^2$) that is less than about 150 ug/cm$^2$.

Also provided is the above medical device, wherein the internal coating, impregnation, or both comprises alexidine at a first concentration (ug/cm$^2$) that is less than about 100 ug/cm$^2$.

Also provided is the above medical device, wherein the internal coating, impregnation, or both, comprises alexidine at a first concentration (ug/cm$^2$) that is less than about 85 ug/cm$^2$.

Also contemplated is the above medical device, wherein the internal coating, impregnation, or both, comprises alexidine at a first concentration (ug/cm$^2$) that is less than about 70 ug/cm$^2$.

Also contemplated is the above medical device, wherein the internal coating, impregnation, or both, comprises alexidine at a first concentration (ug/cm$^2$) that is less than about 60 ug/cm$^2$.

Moreover, what is further provides is the above medical device, wherein the internal coating, impregnation, or both, comprises alexidine at a first concentration (ug/cm$^2$) that is less than about 50 ug/cm$^2$.

Moreover, what is further provides is the above medical device, wherein the internal coating, impregnation, or both, comprises alexidine at a first concentration (ug/cm$^2$) that is less than about 30 ug/cm$^2$.

In embodiments that do not have "about" language, what is provided is the above medical device, wherein the coating, impregnation, or both, comprises alexidine at a concentration (ug/cm$^2$) that is less than 400 ug/cm$^2$, that is less than 300 ug/cm², that is less than 200 ug/cm², that is less than 150 ug/cm², that is less than 100 ug/cm², that is less than about 85 ug/cm², that is less than 80 ug/cm², that is less than about 75 ug/cm², that is less than 70 ug/cm², that is less than 65 ug/cm², 60 ug/cm², 55 ug/cm², 50 ug/cm², 45 ug/cm², 40 ug/cm², 35 ug/cm², 30 ug/cm², and the like. These concentrations can be imposed on external coatings (impregnations, or both), on internal coatings (impregnations, or both), on solutions configured for external coating (impregnation, or both), and on solutions configured for internal coating (impregnation, or both).

The skilled artisan will understand that, where the issue is measuring concentration of alexidine, the concentration will be essentially identical where the concentration (ug/cm²) is that of an "external surface" or is that of an "external coating" or an impregnation that had been applied only at the external surface. When detecting amount (micrograms) of alexidine that is in a "surface" or in a "coating," the result will be the same, because in both cases the same cubic centimeters of area is the focus of the analysis. Impregnation quantities can be measured in terms of micrograms per centimeter squared, for example, by taking a core. The concentration of sub-surface anti-microbial agent can be determined by taking a core sample from the medical device, where the coring device has a constant area at all depths. The ability of acquiring a core sample that has a constant area at all depths is illustrated by borers that are used for taking core samples from trees (see, e.g., Grissino-Mayer (2003) Tree-Ring Research. 59:63-79). Regarding measuring an anti-microbial impregnation, the core sample can be made at a depth that encompasses 10% of the anti-microbial, 20%, 30%, 40%, 50%, 60%, 70%, 80%, 90%, 95%, 98%, 99%, and so on. Where a core sample is taken at a depth that encompasses about 50% of the anti-microbial, for example, statistical methods can be used to acquire the quantity of anti-microbial that corresponds to about 100% of the expected anti-microbial that is present in the impregnation.

Further embraced is the above medical device, wherein (i) the alexidine is capable of reducing a thrombogenic event that takes place on one or both of said external surface and internal surface, and wherein (ii) the alexidine is capable of reducing microbial activity that takes place on one or both of said external surface and internal surface.

In another aspect, what is provided is the above medical device, wherein the external surface comprises alexidine at a concentration ($\mu g/cm^2$) that is capable of reducing thrombogenic events, and wherein said concentration is such that a comparator medical device with an external surface comprising chlorhexidine at the same said concentration is not capable of detectably reducing thrombogenic events.

In yet another aspect, what is provided is the above medical device, wherein the external surface comprises alexidine at a concentration ($\mu g/cm^2$) that is capable of reducing thrombogenic events to a relatively large extent that is in the range of 0-50%, relative to an uninhibited thrombogenic event level defined as 100%, and wherein said concentration is such that a comparator medical device with an external surface comprising chlorhexidine at the same said concentration is capable of reducing thrombogenic events to a relatively small extent that is in the range of 90.0-99.9%, where the uninhibited thrombogenic event level is defined as 100%.

Also provided is the above medical device, wherein the internal surface comprises alexidine at a concentration ($\mu g/cm^2$) that is capable of reducing thrombogenic events to a relatively large extent that is in the range of 0-50%, relative to an uninhibited thrombogenic event level defined as 100%, and wherein said concentration is such that a comparator medical device with an internal surface comprising chlorhexidine at the same said concentration is capable of reducing thrombogenic events to a relatively small extent that is in the range of 90.0-99.9%, where the uninhibited thrombogenic event level is defined as 100%.

Moreover, the present disclosure also embraces the above medical device, wherein the medical device comprises one or more of alexidine, alexidine base, alexidine hydrochloride, alexidine dihydrochloride, alexidine monoacetate, alexidine diacetate, alexidine gluconate, or alexidine digluconate.

Also provided is the above medical device, comprising an inner surface coating, impregnation, or both, that comprises alexidine, and an outer surface coating, impregnation, or both, that comprises alexidine, wherein the inner surface coating, coating, impregnation, or both, comprises a first composition and the outer surface coating, impregnation, or both comprises a second composition, and wherein the first composition is the same as the second composition.

Furthermore, what is provided is the above medical device, wherein the alexidine that is comprised by the medical device is sufficient in concentration to result in a change in blood clotting time of at least 150% (50% increase in blood clotting time), when compared to the clotting time with a control medical device that does not comprise alexidine, as measured using human whole blood. Preferably, but without implying any limitation, clotting using human whole blood is measured using an example from the present disclosure.

Additionally, what is provided is the above medical device, wherein the alexidine that is comprised by the medical device is sufficient in concentration to result in less than 90% of maximal platelet deposition on the medical device, when compared to platelet deposition with a control medical device that does not comprise alexidine (maximal platelet deposition defined as 100%).

In another aspect, what is provided is the above medical device, wherein the alexidine content is one or both of: (i) at least 50 micrograms per cm² of external surface area; and (ii) at least 5 micrograms per cm² of internal surface area.

In another aspect, what is provided is the above medical device, wherein the alexidine content is one or both of: (i) at least 75 micrograms per cm² of external surface area; and (ii) at least 10 micrograms per cm² of internal surface area.

In yet another embodiment, the present disclosure encompasses the above medical device, wherein the alexidine content is one or both of: (i) at least 100 micrograms per cm² of external surface area; and (ii) at least 20 micrograms per cm² of internal surface area.

In another aspect, what is provided is the above medical device, wherein the alexidine content is one or both of: (i) at least 200 micrograms per cm² of external surface area; and (ii) at least 40 micrograms per cm² of internal surface area.

In another aspect, what is provided is the above medical device, wherein the alexidine content is one or both of: (i) at least 300 micrograms per cm² of external surface area; and (ii) at least 100 micrograms per cm² of internal surface area.

In another aspect, what is provided is the above medical device, wherein the alexidine content is one or both of: (i) at least 400 micrograms per cm² of external surface area; and (ii) at least 200 micrograms per cm² of internal surface area.

What is also provided is the above medical device, wherein the alexidine is bulk distributed.

What is further provided is the above medical device that comprises one or more of a catheter, cannula, elongated tube, valve, or implant port.

What is also provided is the above medical device that does not comprise chlorhexidine. Also, what is provided is the above medical device that does not comprise triclosan, does not comprise silver, or does not comprise triclosan and silver.

In polymer embodiments of coatings, impregnations, or both, what is provided is the above medical device that comprises a coating, impregnation, or both, that is a polymer that comprises sulfobetaine, polysulfobetaine, carboxybetaine, polycarboxybetaine, or both sulfobetaine and carboxybetaine, or both Elast-Eon®. Coatings, impregnations, or combinations of coatings and impregnations, that are based on sulfobetaine or carboxybetaine, are applied to the medical device in a distinct manufacturing process.

In another aspect, the present disclosure provides the above medical device that is adapted for contact with or insertion into one or more of the vascular system, the urinary tract, or the respiratory system.

In a method of medical use embodiment, what is provided is a method for storing a medical device in a mammalian subject, wherein the medical device resides at least partly in the lumen of a blood vessel, the method comprising: (i) The step of inserting at least part of the medical device in the blood vessel, followed by, (ii) The step of administering a solution, withdrawing a biological fluid, or administering a solution and also withdrawing a biological fluid, followed by, (iii) The step of withdrawing the medical device from the blood vessel, wherein the medical device comprises a surface that is capable of contacting blood in the vascular system, wherein the medical device comprises an amount of alexidine that is both anti-thrombogenically effective and anti-microbially effective, and wherein in use the alexidine is capable of reducing thrombogenic events and is capable of reducing microbial activity.

In another aspect, what is provided is the above method, wherein the solution is a sterile solution, a pharmacological agent, or a diagnostic agent. Also provided is the above method, wherein the medical device comprises an external surface, and wherein the alexidine content is at least 50 micrograms per $cm^2$ of external surface area, and wherein the alexidine that is comprised by the external surface of the medical device is sufficient to result in a change in blood clotting time of at least 125% (25% increase in blood clotting time), when compared to the blood clotting time with a control medical device that does not comprise alexidine, as measured using human whole blood. Preferably, but without implying any limitation, clotting using human whole blood is measured using an example from the present disclosure.

In a manufacturing method embodiment, what is provided is a method for manufacturing a medical device that comprises alexidine, comprising the steps of: Step i. Acquiring a medical device that comprises an external surface and an internal surface; Step ii. Contacting the external surface with a first solution that comprises alexidine, and contacting the internal surface with a second solution that comprises alexidine, Step iii. Maintaining a contact of the external surface with the first solution for a time sufficient to produce an external surface that comprises alexidine; and maintaining a contact of the internal surface with the second solution for a time sufficient to produce an external surface that comprises alexidine, Step iv. Drying or removing any residual solution from the medical device that comprises alexidine; wherein the medical device that comprises alexidine comprises an amount of alexidine that is both anti-thrombogenically effective and anti-microbially effective.

In another manufacturing aspect, what is provided is the above method, wherein the external surface is contacted with the solution for a first time frame, wherein the internal surface is contacted with the solution for a second time frame, and wherein the first time frame at least partially overlaps the second time frame.

Also provided is a non-overlapping time frame embodiment of the above method, wherein the external surface is contacted with the solution for a first time frame, wherein the internal surface is contacted with the solution for a second time frame, and wherein the first time frame does not overlaps the second time frame.

Also provided is the above manufacturing method, wherein the alexidine concentration of the first solution is not the same as the alexidine concentration as the second solution.

In another aspect of the above manufacturing method, what is provided is the above method, wherein the contacting comprises one or more of dipping, soaking, spraying, or wiping.

Also, the above manufacturing method embraces a method wherein the first solvent comprises one or both of tetrahydrofuran and methanol, or wherein the second solvent comprises one or both of tetrahydrofuran and methanol. Also embraced, is the above method wherein: (i) the first solvent comprises a soluble plastic polymer, (ii) wherein the second solvent comprises a soluble plastic polymer, (iii) wherein the first solvent comprises a soluble plastic polymer and the second solvent comprises a soluble plastic polymer, or (iv) wherein the first solvent does and the second solvent does not contain a soluble plastic polymer.

Methods for storing device in a patient, as might occur during clinical use, are also provided. What is provided is a method for storing a medical device in a mammalian subject, wherein the medical device resides at least partly in the lumen of a blood vessel, the method comprising: (a) The step of inserting at least part of the medical device into the blood vessel lumen, followed by, (b) The step of administering a solution, withdrawing a biological fluid, or both administering a solution and also withdrawing a biological fluid, followed by, (c) The step of withdrawing the medical device from the blood vessel, wherein the medical device comprises a surface that is capable of contacting blood in the vascular system, wherein the medical device comprises an amount of alexidine that is both anti-thrombogenically effective and anti-microbially effective, and wherein in use the alexidine is capable of reducing thrombogenic events and is capable of reducing microbial activity. Also provided is the above method, wherein the solution is a sterile solution, a pharmacological agent, or a diagnostic agent. The device can be stored, that is, permitted to reside in a body cavity, body lumen, blood vessel, urinary tract, lymphatic vessel, and so on, for a period of days, weeks, or months.

In a solution embodiment, what is provided is a solution configured for coating, impregnating, or both, a medical device with alexidine, the solution comprising: (i) at least 0.05% alexidine, (ii) a solvent comprising tetrahydrofuran (THF) and methanol, THF and ethanol, or THF and isopropyl alcohol, and (iii) optionally soluble polyurethane.

The present disclosure encompasses all possible combinations of the above embodiments, and encompasses all possible disclosures of each independent claim with its dependent claims. For example, what is encompassed is an invention that is the combination of: Claim 1+Claim 2; or the combination of: Claim 1+Claim 2+Claim 3; or the combination of Claim 1+Claim 3+Claim 4; or the combination of Claim 1+Claim 2+Claim 3+Claim 4; and the like.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

The terms "adapted to," "configured for," and "capable of," mean the same thing. Where more than one of these terms are used in a claim set, it is the case that each and every one of these terms, as they might occur, means, "capable of."

DETAILED DESCRIPTION

Proximal and Distal

Figure 1:
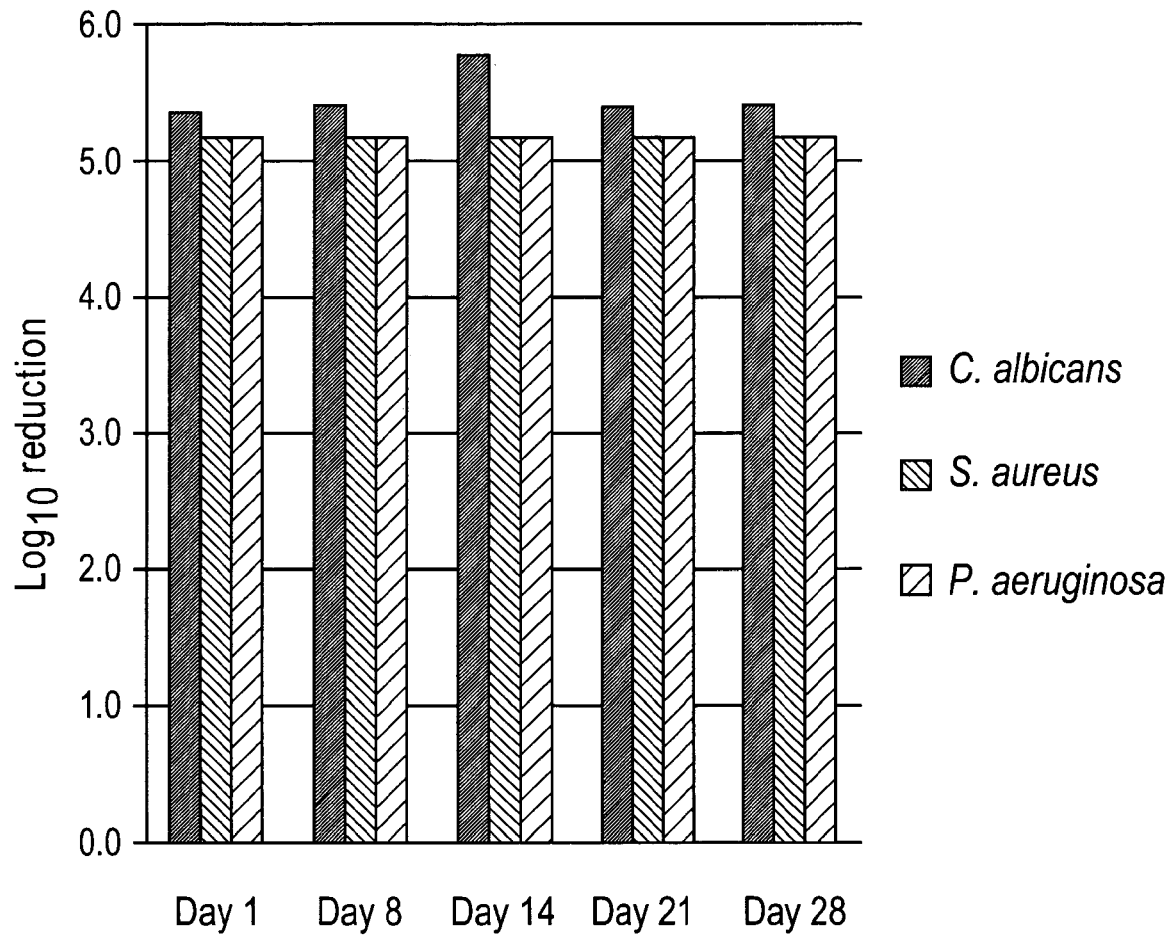
FIG. 1 discloses microbial growth data that demonstrates broad spectrum antimicrobial efficacy of alexidine-treated peripherally inserted central catheters (PICCs).

In the context of a medical device, such as an assembly having a longitudinal aspect, for example, an assembly of a sheath and dilator, the term "proximal" refers generally to the end of the assembly that is closest to the physician while "distal" refers generally to the end that is inserted into the patient. Where the terms "proximal-to-distal movement" or "proximal-to-distal force" are used, these terms can refer to the context where the device is being used with the patient, and also in an abstract context, where a physician and patient are not present.

Treating, Coating, and Impregnating Medical Devices

Treating of medical devices may include coating, impregnating, a combination of coating and impregnating, and surface-initiated polymerization. Coating and impregnation are distinguished. Generally, coating resides on, or adheres to, the exterior surface of a medical device. Coating thickness can be, without limitation, about 1 nanometers (nm), about 2 nm, about 5 nm, about 10 nm, about 20 nm, about 50 nm, about 100 nm, about 500 nm, about 1.0 micrometers (um), about 10 um, about 50 um, about 100 um, about 500 um, about 1 millimeters (mm), and so on, extending about the surface of the medical device. Material used for coating can extend into the medical device, and this aspect of the coating can be referred to as an impregnation. Impregnation can extend, without limitation, about 10 nanometers (nm), about 50 nm, about 100 nm, about 500 nm, about 1.0 micrometers (um), about 10 um, about 50 um, about 100 um, about 500 um, about 1 millimeters (mm), and so on, from the surface into core of medical device. Use of the term "coating" or "impregnation" can depend on whether the coating or the impregnation is functionally more important. Alternatively, and without implying any limitation, the term "coating" can be used where the quantity, in terms of weight or in terms of number of molecules, of anti-microbial agent is substantially located on the surface, and insubstantially located within the solid portion of the medical device. Also, the term "impregnation" can be used where the anti-microbial agent is substantially located within the solid portion of the medical device, and where the quantity bound to the surface is relatively insubstantial.

Surface-Initiated Polymerization

Surface initiated polymerization on a device surface utilizes initiators and catalyst(s) to polymerize a thin layer on the surface which can extent outward from the surface of medical device, without limitation, about 10 nanometers (nm), about 50 nm, about 100 nm, about 500 nm, about 1.0 micrometers (um), about 10 um, about 50 um, about 100 um, about 500 um, about 1 millimeters (mm), and so on.

An anti-microbial agent that is coated, can be bound to a polymer matrix by ionic bonds, by hydrophilic interactions, by lipophilic interactions, by a combination of hydrophilic and lipophilic interactions, by Van der Waals forces, by covalent binding, and the like, or any combination thereof. An anti-microbial agent that is impregnated, can be bound to a polymer matrix by ionic bonds, by hydrophilic interactions, by lipophilic interactions, by a combination of hydrophilic and lipophilic interactions, by Van der Waals forces, by covalent binding, and the like, or any combination thereof.

Alternatively, device can be manufactured so that an agent does not reside on the outer most surface, but resides in the interior layers of medical device. This could be achieved by treating further the external surface of the device coated or impregnated with alexidine with a solution containing 0.05%, 0.1%, 0.2%, 0.5%, 1.0%, 1.5%, 2.0%, 2.5%, 3.0%, 3.5%, 4.0%, 4.5%, 5.0%, 6.0%, 7.0%, 8.0%, 9.0%, greater than 10%, and the like, of soluble polymer, such as soluble polyurethane. Alternatively, this could be achieved by washing the impregnated device with a solvent that substantially removes externally-bound anti-microbial agent, and that has relatively little influence on removing internally-bound anti-microbial agent.

Bulk Distribution

The term "bulk distributed" can refer to the distribution of anti-microbial agent, that is characteristic of that obtained with bulk manufacturing methods. The distribution can be expressed in terms of, e.g., average distance between individual molecules of anti-microbial agent, or to some other statistical parameter that describes the distances between individual molecules of anti-microbial agent. Bulk distribution can include, without limitation, mixing creating the polymer from monomers in the presence of anti-microbial agent, adding the anti-microbial agent to melted polymer, adding the anti-microbial agent to crushed solid polymer, adding the anti-microbial agent to polymer beads, and so on. An impregnation that extends throughout entire medical device, and where extension throughout device is substantially uniform in 3-dimensional distribution, the impregnation can be characterized as a bulk distribution.

External Surface

A coating that is associated with an "external surface" of a medical device can be a coating where, e.g., atoms or molecules of the coating are substantially located on the exterior of the medical device, for example, where the atoms or molecules are associated by way of adhesion or physisorption or chemisorption to sites within the medical device that are essentially at the exterior surface. Also, a coating that is associated with an "external surface" of a medical device can be a coating where, e.g., atoms or molecules of the coating are located essentially at the exterior surface of the medical device by way of absorption (adsorbed) to sites within the medical device that are essentially at the exterior surface and also at deeper sites of absorption, for example, at depths of up to 50 micrometers (um), up to 100 um, up to 200 um, up to 500 um, up to 1,000 um (1 mm), up to 2 mm, up to 5 mm, and so on. Preferably, but without limitation, where a coating encompasses anti-microbial agent located below the surface of medical device, the anti-microbial agent is bound to the surface areas within pores, cavities, crevices, and such.

Internal Surface

A coating that is associated with an "internal surface," such as a luminal surface or the surfaces of a cavity, can be that where atoms or molecules, are associated by way of adsorption (molecular interactions mainly with the surface of the lumen), impregnation, or by a combination of adsorption and impregnation. Where a coating, or a component of a coating, is adsorbed, the molecular interaction can be covalent, non-covalent, or a mixture thereof. Also, where a coating, or a component of a coating, is absorbed (impregnated), the molecular interaction can be covalent, non-covalent, or a mixture thereof.

Relative Alexidine Concentrations of External Versus Internal Solutions

A first solution used to apply the external coating (or external impregnation, or combination of external coating and external impregnation) can contain alexidine that is at a greater concentration than a second solution used to confer the internal coating (or internal impregnation, or combination of internal coating and internal impregnation), where the concentration in the first solution is at least 1.5-fold greater, at least 2.0-fold greater, at least 2.5-fold greater, at least 3.0-fold greater, at least 3.5-fold greater, at least 4.0-fold greater, than that of the second solution.

An external coating (or external impregnation, or combination of external coating and external impregnation) can contain alexidine that is at a greater concentration than in an internal coating (or internal impregnation, or combination of internal coating and internal impregnation), where the concentration in the external coating is at least 1.5-fold greater, at least 2.0-fold greater, at least 2.5-fold greater, at least 3.0-fold greater, at least 3.5-fold greater, at least 4.0-fold greater, than that of the internal coating.

Regarding the Terms "Surface" and "Coating"

Alexidine in an external coating or in an internal coating, of a coated medical device, can be measured to a depth of 0.10 mm, 0.20 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, 3.0 mm, and so on. An internal coating, for example, can reside on the surface of a lumen or on the surface of a cavity.

The amount of a chemical or composition present in a coating that is mainly adsorbed (surface-coated), mainly impregnated, or that is a combination adsorption and impregnation, the amount can be measured as follows. A one centimeter squared surface area can be cut out from the catheter, resulting in a piece that is roughly cubic in shape, where one of the faces of the cube is one centimeter squared. The entire cube can then be dissolved for analysis.

Also, a one centimeter long tubing can be cut out from the catheter, resulting in a piece that is roughly 0.8 square centimeter in surface area. The entire tube can then be dissolved for analysis.

This method of analysis is suitable for measuring amounts that are only surface-coated, that are only impregnated, or for measuring amounts that are a combination of these. Where a coating procedure mainly results in adsorption (surface-coating), the quantity that is detected can be expressed in term of a unit that is weight of chemical per area, weight of chemical per volume, or weight of chemical per weight of catheter. Where a coating procedure results in substantial impregnation, or where the coating procedure results in bulk distribution, then a preferred unit is weight of chemical per volume, or weight of chemical per weight of catheter. Surface areas can also be, for example, one square millimeter, and volumes can be, for example, one cubic millimeter. The area need not have a square conformation, but it can be round, amorphous, and so on.

Regarding depth of penetration of alexidine (or chlorhexidine) in a coating, a preferred coating thickness is about 0.2 micrometers (um), about 0.5 um, about 1.0 um, about 2.0 um, about 5.0 um, about 10.0 um, about 20 um, about 30 um, about 40 um, about 50 um, about 60 um, about 70 um, about 80 um, about 100 um, about 120 um, about 140 um, about 160 um, about 180 um, about 200 um, about 300 um, about 400 um, about 500 um, and so on. For internal coating (e.g., coating the surface of a lumen or cavity), a preferred coating depth is 0.2-1.0 micrometers. For external coating, a preferred coating depth is 2-5 micrometers. Where anti-microbial surface occurs substantially on the surface and also occurs substantially at a penetrated depth, the medical device is preferably characterized as one that comprises a coating and also an impregnation.

For external coating, a preferred, non-limiting alexidine content can be about 120-200 micrograms/cm$^2$ (ug/cm$^2$). In embodiments, alexidine content in external coating can be at least 50 ug/cm$^2$, at least 60 ug/cm$^2$, at least 70 ug/cm$^2$, at least 80 ug/cm$^2$, at least 90 ug/cm$^2$, at least 100 ug/cm$^2$, at least 120 ug/cm$^2$, at least 140 ug/cm$^2$, at least 160 ug/cm$^2$, at least 180 ug/cm$^2$, at least 200 ug/cm$^2$, at least 200 ug/cm$^2$, at least 240 ug/cm$^2$, at least 260 ug/cm$^2$, at least 280 ug/cm$^2$, at least 300 ug/cm$^2$, and so on.

For internal coating, a preferred, non-limiting alexidine content can be about 4-70 micrograms/cm$^2$ (ug/cm$^2$). In embodiments, alexidine content in internal coating can be at least 1 ug/cm$^2$, at least 5 ug/cm$^2$, at least 10 ug/cm$^2$, at least 20 ug/cm$^2$, at least 40 ug/cm$^2$, at least 60 ug/cm$^2$, at least 80 ug/cm$^2$, at least 100 ug/cm$^2$, at least 120 ug/cm$^2$, at least 140 ug/cm$^2$, at least 160 ug/cm$^2$, at least 180 ug/cm$^2$, at least 200 ug/cm$^2$, at least 220 ug/cm$^2$, at least 240 ug/cm$^2$, at least 260 ug/cm$^2$, and the like.

What is also provided is the combination of medical device and a formulation, for example, combinations where medical device is being soaked in formulation, where medical device is being partially or fully submersed in a formulation, or where medical device is being perfused with a formulation. Present disclosure provides combination of a medical device with the formulation of one or both of the above formulations. This refers to formulations that do not include polyurethane, as well as to formulations that do include polyurethane.

Bulk Distribution

A material can be bulk-distributed throughout a medical device. A bulk-distributed material, substance, chemical, or chemical composition, can be present at the exterior surface and at all points deeper than the exterior surface. The present disclosure provides a medical device with a bulk-distributed substance, where the substance also adheres to the exterior of the bulk-distributed medical device. Alternatively, the present disclosure also provides a medical device with a bulk-distributed substance, where most or all of the substance that adheres to the exterior of the bulk-distributed medical device is removed by washing in an appropriate solution, for example, a salt solution. In an exclusionary embodiment, the present disclosure can exclude devices that comprise a bulk-distributed compound, such as bulk-distributed chlorhexidine, or some other bulk-distributed anti-microbial.

For bulk distribution, an anti-microbial agent can be covalently bound to a monomer, or to a polymer, or to a cross-linking agent that cross-links polymers.

In non-limiting embodiments, the present disclosure provide a medical device, or other instrument or device, where alexidine is bulk distributed. Bulk distribution within a plastic polymer or rubber, for example, can be accomplished by soaking for a period of time sufficient to allow substantially uniform distribution throughout the device. Alternatively, bulk distribution can be accomplished by including the alexidine in the slurry, powder, viscous solution, of polymer, prior to forming the solid device, for example, prior to or during thermosetting, compression molding, injection molding, extrusion, foaming with a blowing agent, and so on (see, e.g., Brazel and Rosen (2012) Fundamental Principles of Polymeric Materials, $3^{rd}$ ed., Wiley, New York, NY).

In embodiments, the disclosure encompasses methods for bulk distribution, gradient distribution, and limited surface distribution. Methods for manufacturing medical devices where an agent is bulk distributed, gradient distributed, or limited surface distributed, are available (see, e.g., U.S. Pat. No. 4,925,668 issued to Khan, et al, U.S. Pat. No. 5,165,952 issued to Solomon and Byron, and U.S. Pat. No. 5,707,366 issued to Solomon and Byron, all of which are incorporated herein by reference). In some aspects, the disclosed device excludes embodiments with bulk distribution.

Alexidine that is bulk-distributed can be measured by dissolving the entire medical device, precipitating the polymer, and quantifying alexidine by standard methods, such as HPLC.

Extrusion

The present disclosure provides medical devices, such as medical devices that comprise a tubular member, that are treated by way of extrusion. In extrusion, a molten, homogenous thermoplastic material is applied through a die directly on a solid surface, such as a medical device made of a plastic polymer. See, e.g., U.S. Pat. No. 5,328,698 of Onwumere, which is hereby incorporated by reference in its entirety. In a preferred extrusion embodiment, alexidine is added to the polymer at the time of extruding the catheter tubing, thereby minimizing heat-induced degradation.

Treatment of Inside Surface Versus Treatment of Outside Surface

The present disclosure provides a medical device, such as a device comprising a tubular member with an inside surface (cavity; lumen) and an outside surface, where the inside surface comprises a first coating, where the outside surface comprises a second coating, and where the composition of the first coating is not the same as that of the second coating. For example, the disclosure encompasses a catheter where the inside coating has a different concentration of alexidine than that of the outside coating. In methods embodiments, what is provided is a method for coating or impregnating a medical device, the medical device comprising an inside surface, and a cavity or lumen that is defined by said inside surface, wherein the medical device further comprises an outside surface or exterior surface, wherein the method comprises contacting a first formulation to the inside surface, and contacting a second formulation to the outside surface, and where the first and second formulations have a different composition from each other. The concentration of alexidine in the inside coating versus outside coating can differ by at least 1.25-fold, at least 1.5-fold, at least 2.0-fold, at least 2.5-fold, at least 3.0-fold, at least 3.5-fold, at least 4.0-fold, at least 5.0-fold, and so on. Also, the concentration of alexidine used in treatment formulation used for the inner coating can be different from the concentration of alexidine in treatment formulation used for the outside coating, where these concentrations can differ by at least 1.25-fold, at least 1.5-fold, at least 2.0-fold, at least 2.5-fold, at least 3.0-fold, at least 3.5-fold, at least 4.0-fold, at least 5.0-fold, and so on.

A plurality of treatment cycles can be used, for example, one, two, three, four, five, or more treatment cycles. Medical device can be allowed to dry between each treatment cycle, or alternatively, treatment cycles can be conducted without drying, or can be conducted with partial drying.

Dipping and Wiping

In time embodiments, method of treatment of medical device with formulation comprises contacting medical device with formulation for 30 seconds or less, 60 seconds or less, 2 min or less, 4 min or less, 6 min or less, 8 min or less, 10 min or less, 15 min or less, 20 min or less, 30 min or less, 40 min or less, 50 min or less, 60 min or less, 2 h or less, 3 h or less, 4 h or less, and the like. Other time embodiments include 30-60 sec, 1-2 min, 2-4 min, 1-4 min, 1-5 min, 5-10 min, 5-20 min, 10-60 min, and the like. The present disclosure provides for contacting, treating, dipping, coating, impregnating, and also provides a time that ensures that one or both of an anti-microbially effective amount, or an anti-thrombogenically effective amount, of alexidine is coated or impregnated.

In other time embodiments, external treating time is less than 10 seconds, less than 8 sec, less than 6 sec, less than 4 sec, less than 3 sec, less than 2 sec, less than 1 sec, less than 0.8 sec, less than 0.6 sec, less than 0.4 sec, and so on, where a thin, uniform layer of solution is applied to the exterior, and immediately starts to dry. Timing of internal treating can be controlled by pressurized blow-out, to remove solvent from interior of medical device. Internal treating time is about 4 seconds, about 6 sec, about 8 sec, about 10 sec, about 12 sec, about 14 sec, about 16 sec, about 18 sec, about 20 sec, about 25 sec, about 30 sec, about 40 sec, about 60 sec, about 90 sec, about 2 min, about 4 min, about 6 min, about 8 min, about 10 min, and so on.

Without implying any limitation, "dipping" refers to an act where a device is submerged, either partially or completely, in a bath for a relatively short period of time, for example, a fraction of a second, for a few seconds, or for under a minute. After dipping, there may or may not be residual bath solution on the device, and there may or may not be continued migration of solutes or solvents from the residual bath solution into the device. Without implying any limitation, "soaking" refers to an act where a device is submerged, either partially or completely, in a bath for a relatively long period of time, for example, over one minute, over one hour, from 8-10 hours, from 10-15 hours, from 15-20 hours, and so on. "Wiping" refers to an act where a device is contacted with a solution by way of drawing a cloth, fabric, or matrix, over the device, where the cloth, fabric, or matrix, has been impregnated with the bath solution. Without implying any limitation, any residual solution is minimal with wiping, as opposed to that with dipping or soaking.

Treating Interior Surface Versus Exterior Surface

In embodiments where an interior is treated with a first formulation (A) and an exterior is treated with a second formulation (B), contact of the interior by the first formulation (A) and contact of the same interior by the second formulation (B) occurs, in some embodiments, at a ratio of greater than (A)/(B)=80/20, greater than (A)/(B)=85/15, greater than (A)/(B)=90/10, greater than (A)/(B)=95/5, greater than (A)/(B)=98/2, greater than (A)/(B)=99/1, greater than (A)/(B)=99.9/0.1, and so on. What is also contemplated, are embodiments where an exterior is treated with a first formulation (C) and an interior is treated with a second formulation (D), contact of the exterior by the first formulation (C) and contact of the same exterior by the second formulation (D) occurs, in certain embodiments, at a ratio of greater than (C)/(D)=80/20, greater than (C)/(D)=85/15, greater than (C)/(D)=90/10, greater than (C)/(D)=95/5, greater than (C)/(D)=98/2, greater than (C)/(D)=99/1, greater than (C)/(D)=99.9/0.1, and so on. These ratios can refer, for example, to contact time, to relative concentration of a specific solute, to relative concentrations of alexidine, to relative concentration of a specific solvent, and so on. In exclusionary embodiments, what can be excluded is a medical device, or a method of treating, where the ratio falls into one of the above-disclosed parameters.

The following terminology is for use in describing the concentration of any agent, for example, an anti-microbial agent, in a medical device, such as a catheter, or a related composition. The medical device has an external surface portion, and an internal volume portion, where a representational part of the internal volume comprises an area of the external surface portion.

A selected representational part of the internal volume, for example, when sampled from the outer surface of a catheter or from an internal lumen of a catheter, contains the agent at a concentration of at least 5 micromolar (5 uM), at least 10 uM, at least 20 uM, at least 40 uM, at least 60 uM, at least 80 uM, at least 100 uM, at least 120 uM, at least 140 uM, at least 160 uM, at least 180 uM, at least 200 uM, at least 300 uM, at least 400 uM, at least 600 uM, at least 800 uM, at least 1000 uM (1.0 mM), at least 2 mM, at least 5 mM, at least 10 mM, at least 15 mM, at least 20 mM, at least 25 mM, at least 30 mM, at least 40 mM, at least 60 mM, at least 80 mM, at least 100 mM, at least 150 mM, at least 200 mM, at least 250 mM, and the like. In this context, the concentration unit of molarity is a surrogate for concentration of moles of agent per 100 cubic centimeters (one liter) of the selected internal volume of the medical device. In this context, "internal volume" refers to the solid material within the plastic wall of the medical device. For example, this solid material can be that which extends from a square centimeter of surface and down to a depth of 1 mm below the surface, where the volume would be 1 cm×1 cm×0.1 cm. In this context, "internal volume" does not refer to any volume within the lumen of the medical device.

The disclosure encompasses a medical device treated with one or more of the presently described formulations, where the formulation contains a small molecule, a pharmaceutically active macromolecule, an anti-microbial agent, an anti-thrombogenic agent, and so on. For measurement, the entire medical device can be subjected to solvent extraction. Alternatively, a representative sample can be cut out, by way of a sample that has a conformation that is cubical, rectangular, cylindrical, or amorphous, as long as the sample is believed to be representative of the distribution (or concentration) of the agent in the region between the external surface and selected depth, for example, to 0.1 mm deep, to 0.5 mm deep, to 1.0 mm deep, to 2.0 mm deep, to 5.0 mm deep, and so on. Alternatively, the sample can be taken from a region entirely below the surface, for example, in a region between 0.05 mm deep and 0.20 mm deep, or in a region between 1.0 mm deep and 2.0 mm deep, and so on.

Where an agent binds only to the surface of a medical device, that is, by adhering (or adsorbing) to the outside surface (including to the outside surface of any microscopic pores or microscopic channels that happen to reside on the external surface), documentation of data on treating may be more meaningfully expressed in terms of micrograms of the agent per square millimeter (and less meaningfully expressed in terms of micrograms agent per cubic millimeter). The present disclosure provides anti-microbial polymers (see, e.g., Tew et al (2010) Acc. Chem. Res. 43:30-39), e.g., in combination with an alexidine coating, impregnation, or combination of coating and impregnation.

Anti-Thrombogenic Amounts and Anti-Microbial Amounts

Without implying any limitation, "anti-thrombogenically effective" amount encompasses an amount that reduces some aspect of blood clotting to less than 100% of a maximal value, to less than 95% of a maximal value, to less than 90% of a maximal value, to less than 85% a maximal value, to less than 80%, to less than 75%, to less than 70%, to less than 65%, to less than 60%, to less than 55%, to less than 50%, to less than 40%, to less than 30%, to less than 20%, to less than 10%, to less than 5%, to less than 2%, to less than 1%, of the maximal value, and so on.

Anti-thrombogenic activity can be measured by assays that are entirely in the fluid phase, by assays that detect the formation of a blood clot, by assays using a chromogenic substrate, by assays that detect that activation of specific blood clotting proteins such as the conversion of prothrombin to thrombin, by assays for platelet activation, and so on. Without implying any limitation, "thrombogenic event" encompasses one or more of, formation of a blood clot, activation of platelets, conversion of thrombin to prothrombin, catalytic cleavage of a chromogenic substrate, cleavage of one or more of the activation peptide bonds in prothrombin, activation of factor X, conversion of fibrinogen to fibrin, and so on.

Anti-thrombogenic activity of a device comprising alexidine can be measured with animal models, by determining the weight of thrombus per unit length of the medical device, by determining the length of thrombus covering the medical device, by determining the thickness and nature of thrombus based on gross histo-pathological observations. Methods for determining blood clot formation, platelet adhesion, platelet aggregation, to surfaces of catheters are available. These methods include electron microscopy (see, e.g., Gao et al (2013) Int. J. Clin. Exp. Med. 6:259-268; Kallmes et al (1997) Am. J. Neuroradiol. 18:1243-1251; Wildner et al (1978) Circulation Res. 43:424-428). Without implying any limitation, the present disclosure provides assays, e.g., activation partial thrombin time (APTT), thrombin time (TT), prothrombin time (PT), fibrinogen time (FT), and so on.

Without implying any limitation, "anti-microbially effective" amount means an amount that reduces colonization by microbes by at least $1.0 \log_{10}$ of the initial challenge concentration, by at least $2.0 \log_{10}$ of the initial challenge concentration, by at least $3.0 \log_{10}$ of the initial challenge concentration, by at least $4.0 \log_{10}$ of the initial challenge concentration, by at least $5.0 \log_{10}$ of the initial challenge concentration, by at least $6.0 \log_{10}$ of the initial challenge concentration, and so on. "Anti-microbially effective" amount also means an amount of alexidine that reduces colonization by microbes by at least $1.0 \log_{10}$ to $10 \log_{10}$ compared to the colonization on a control device comprising without alexidine.

Anti-microbial activity can be measured, for example, by assays that are entirely in the fluid phase, by assays on agar, by assays where a medical device treated with an anti-microbial is tested, by assays where a medical device impregnated with an anti-microbial is tested, and so on. Without implying any limitation, "microbial activity" encompasses one or more of, colony formation, increase in number of microbial cells by cell division, increase in cell number by migration or chemotaxis, metabolic rate such as oxidation of glucose or glucose fermentation, biofilm formation, and the like.

Polymers for Applying a Coating, Impregnation, or Both Coating and Impregnation, to a Medical Device; Polymers of Treatable Medical Devices In a non-limiting embodiment, coating (or impregnation, or combination of coating and impregnation) with a solution that contains a dissolved polymer, e.g., dissolved polyurethane, is preferred only for external coating, and not for internal coating, in order to avoid interactions between a guidewire and any internal coating. The following list of polymers also serves to identify the chemical composition that is comprised by a coatable medical device. In other words, the polymeric component of a coatable medical device of the present disclosure can be comprises partially, mainly, or entirely, of polyurethane, polyethylene, polysiloxane, or any of the other polymers as disclosed herein.

What is embraced is a formulation for applying to a surface of a medical device, for example, by soaking, where the formulation comprises a dissolved plastic polymer. The dissolved plastic polymer can be more or more of, or any combination of, polyurethane, polyethylene, polyethlyene teraphthalate, ethylene vinyl acetate, silicone, tetrafluoroethylene, polypropylene, polyethylene oxide, polyacrylate, and so on. What is encompassed are coatings, coating solutions, impregnation solutions, or solutions used for both coating an impregnating, and medical devices that are coated with coating or impregnating solutions, using Carbothane® family of polycarbonate-based aliphatic and aromatic polyurethanes, Estane®, which is a thermoplastic polyurethane, Pellethane®, which is a family of medical-grade polyurethane elastomers and exceptionally smooth surfaces, Tecoflex®, which is a family of aliphatic polyether polyurethanes, where low durometer versions are particularly suitable for long-term implant applications, Tecothane®, an aromatic polyurethane, Texin®, an aromatic polyether-based polyurethane which allows for very thin gauges (Microspec Corp., Peterborough, NH; Lubrizol, Inc., Wickliffe, Ohio; Entec Polymers, Orlando, FL). See, U.S. Pat. No. 6,565,591 of Brady, U.S. Pat. No. 7,029,467 of Currier, and U.S. Pat. No. 7,892,469 of Lim, Elast-Eon™ polymers (AorTech International, Rogers, MN) which are co-polymer of silicone macrodiols and polyurethanes which are extremely biostable, and thereby used in long term implants (See, US 2009/0118455 A1 and WO/2000/064971 of Gunatillake, U.S. Pat. Nos. 6,627,724; 6,313,254; WO/1998/013405 of Gunatillake, which are hereby incorporated by reference in their entirety. In embodiments, the present disclosure provides the recited polymers for use in treatment solutions, or for use in manufacturing the medical device that is to be coated, impregnated, or both coated and impregnated, or subject to other types of modifications.

Soluble polymer is more preferred for external treatment, and less preferred for internal treatment, because internal soluble polymer may narrow the lumen if not blown out completely during the treatment process. In some embodiments, what is provided is an internal treatment that does, in fact, include soluble polymer.

The disclosed polymers can be used for manufacturing a medical device itself, as well as for coating the manufactured medical device and for impregnating the manufactured medical device.

Copolymers are encompassed by the disclosure, for example, copolymers of the block type, the random type, and copolymers of the rake type (see, e.g., U.S. Pat. No. 8,008,407 of Oberhellman et al, and U.S. Pat. No. 8,084,535 of Maton et al, which are incorporated herein by reference in their entirety). Because of their weak, rubbery mechanical properties, polysiloxane is sometimes prepared as chemically crosslinked, or synthesized as a block polymer that alternates with a harder type of polymer (see, page 36 of F. Wang (1998) Polydimethylsiloxane Modification of Segmented Thermoplastic Polyurethanes and Polyureas, Thesis, Virginia Polytechnic Institute and State Univ., Blacksburg, VA).

In soluble polymer embodiments, what is provided is a formulation containing about 0.0%, about 0.1%, about 0.2%, about 0.5%, about 1.0%, about 1.5%, about 2.0%, about 2.5%, about 3.0%, about 3.5%, about 4.0%, about 4.5%, about 5.0%, about 6.0%, about 7.0%, about 8.0%, about 9.0%, about 10%, and the like, of soluble polymer, such as soluble polyurethane. In other aspects, what is provided is a formulation with greater than 0.2%, 0.5%, 1.0%, 1.5%, 2.0%, 2.5%, 3.0%, 3.5%, 4.0%, 4.5%, 5.0%, 6.0%, 7.0%, 8.0%, 9.0%, greater than 10%, and the like, or lesser than 0.2%, 0.5%, 1.0%, 1.5%, 2.0%, 2.5%, 3.0%, 3.5%, 4.0%, 4.5%, 5.0%, 6.0%, 7.0%, 8.0%, 9.0%, lesser than 10%, and the like, of soluble polymer.

Soaking, Dipping, and Bulk Distribution

For treating external surface or internal surface of medical device, preferred solvents include THF/methanol, DMF/methanol, THF/ethanol, THF/IPA, or IPA alone. For bulk distribution, IPA is an acceptable solvent for introducing alexidine into medical device. Alternatively, for bulk distribution, alexidine can be added to the resin for compounding or extrusion.

Penetration of Alexidine into Medical Device

Treatment conditions for an external surface, or for an internal surface, e.g., luminal surface, can result in at least 90% of the taken-up alexidine residing within 0.01 millimeters (mm) from the surface, at least 90% of alexidine residing within 0.05 mm from the surface, at least 90% of alexidine residing within 0.10 mm from the surface, at least 90% of alexidine residing within 0.5 mm from the surface, at least 90% of alexidine residing within 1.0 mm from the surface, at least 90% of alexidine residing within 5.0 mm from the surface, at least 90% of alexidine residing within 10.0 mm from the surface, and so on.

The viscosity of solutions and formulations, including those comprising polyurethane can be measured using available instruments and methods. See, for example U.S. Pat. No. 8,017,686 issued to Buter, et al, and U.S. Pat. No. 5,091,205 issued to Fan, which are hereby incorporated by reference. The Brookfield viscometer is a standard instrument (Brookfield Engineering Laboratories, Middleboro, MA). Equipment and methods for burst tests are available. See, e.g., Uson Testra static burst tester; Uson, Houston, Texas. The burst test can be destructive or non-destructive.

Extracting Catheters and Dissolution of Medical Devices, Such as Catheters

Extracting catheters, for example, for quantifying the content of alexidine, can be carried out as follows. First, the catheter or other medical device is soaked with 100% methanol, or a solvent mixture containing methanol and acetonitrile. Extraction time is 30 minutes or more. Then, the solution containing the alexidine is diluted into a large amount of water, and then used for analysis. The dilution can be, for example, 10-fold, 100-fold, 1000-fold, and so on. Dissolution of catheters for quantifying the content of alexidine, can be carried out by dissolving the medical device or a segment of the medical device with 100% tetrahydrofuran (THF), then precipitating the polymer with 50% methanol and 50% water, and the solution is analyzed with techniques such as HPLC, or microbiological assays.

Alexidine can be provided in non-ionized form, or can be provided as a salt. Anions suitable for use in a salt include chloride such as alexidine hydrochloride and alexidine dihydrochloride; acetate such as alexidine acetate and alexidine diacetate; gluconate such as alexidine gluconate; and other salt forms including, glutamic acid, aspartic acid, fumarate, tartarate, citrate, borate, formate, bromide and so on. Solvents suitable for initial solubilization of an agent, as well as for dilution of the initially solubilized agent, can comprise one or more of tetrahydrofuran (THF), methanol, ethanol, isopropyl alcohol (IPA), methyl-ethyl-ketone (MEK), acetone, acetonitrile, dimethylether, methylethylether, methylene chloride, methyl acetate, ethyl acetate, isopropyl acetate, water, and the like. In a multi-component solvent solution, each solvent can occur at a concentration of 0.01-0.1%, 0.1-0.2%, 0.1-0.5%, 0.1-1.0%, 1.0-2.0%, 1.0-5.0%, 5-10%, 10-20%, 20-30%, 30-40%, 40-50%, 50-60%, 60-70%, 70-80%, 80-90%, 90-99%, or any combination thereof, such as 5-20%. Without implying any limitation, medical device of the present disclosure can be extracted with, for example, (i) Tetrahydrofuran; (ii) Tetrahydrofuran plus methanol; (iii) Isopropyl alcohol (IPA); (v) Methyl acetate, or any combination of these. Where medical device has a lumen or any interior cavity, extraction can be separately conducted on external surface and internal surface. Guidance on exposing only an internal surface of a catheter to a solution, without exposure to external surface, is available, for example, from descriptions of catheters that have "locking solutions" (see, e.g., Lok et al (2007) Nephrol. Dial. Transplant. 22:477-483). Extraction of only an internal or luminal surface, or of only an external surface, can utilize exposure to a solvent for 30-60 seconds, 1-2 min, 5-10 min, about 2 min, about 5 min, about 10 min, about 20 min, about 30 min, about 60 min, about 2 hours, and the like. The solvent, and extraction time, can be sufficient to extract at least 80%, at least 85%, at least 90%, at least 95%, of alexidine from the surface of a medical device such as a catheter.

Surface extraction conditions can extract at least 90% of alexidine that resides within 0.01 millimeters (mm) from the surface, at least 90% of alexidine that resides within 0.05 mm from the surface, at least 90% of alexidine that resides within 0.10 mm from the surface, at least 90% of alexidine that resides within 0.5 mm from the surface, at least 90% of alexidine that resides within 1.0 mm from the surface, at least 90% of alexidine that resides within 5.0 mm from the surface, at least 90% of alexidine that resides within 10.0 mm from the surface, and so on.

Total alexidine content can be measured by dissolving the entire medical device with a solvent and precipitating the polymer from the solution, and measuring the amount of extracted or dissolved alexidine. Internal alexidine content can be measured by determining the amount of external alexidine, determining the total content by dissolving entire medical device, and subtracting. By dissolving the "entire medical device," what is preferred is dissolving only the relevant part of the medical device, for example, dissolving a segment of a catheter that is sliced out of the tubular portion of the catheter using a knife.

Efficacy of a treatment procedure can be assessed by extracting the coated device, followed by measuring the extracted agent. The agent can be, for example, an anti-microbial or anti-thrombogenic agent. The agent can be extracted and solubilized in water, physiological saline, or some other aqueous solution. The agent can be extracted and solubilized in a solvent such as tetrahydrofuran (THF), dimethylether, acetone, dimethylsulfoxide (DMSO), methanol, chloroform, or a mixture thereof, including mixtures that include water. After solubilization, the solution is optionally dispersed into an aqueous solution, dispersed in an aqueous solution with sonication, or dispersed into an aqueous solution by associating with albumin. Where the anti-microbial agent resides in the surface of, or has been impregnated into, or has been bulk incorporated into, a medical device, the agent can be extracted from the device using a solvent, or crushed or pulverized, and then extracted with solvent. Where extraction efficiency is less than about 99%, the medical device can be subjected to two or more repeated extractions, followed by combining the solutions used for these extractions.

Solubilized or extracted anti-microbial can be measured using chemical methods, e.g., high-performance liquid chromatography (HPLC). Alternatively extracted agent can be measured by way of biological methods, e.g., microbiological assays (in solution or agar-based) or assays sensitive to inhibition of some aspect of the blood clotting cascade or platelet activation cascade.

Rates of Diffusion or Elution

Rate of release of alexidine from a medical device can be measured using HPLC, or using labeled alexidine, such as [$^3$H]alexidine or [$^{14}$C]alexidine. A composition that is "labeled" is detectable, either directly or indirectly, by spectroscopic, photochemical, biochemical, immunochemical, isotopic, or chemical methods. Useful labels include $^{32}$P, $^{33}$P, $^{35}$S, $^{14}$C, $^3$H, $^{125}$I, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

Compositions and Dimensions of Medical Device

Thermoplastic polyurethane (TPU) tubing, resins, and the like, are available for use in the present disclosure, for example, for manufacturing the medical device, for treating a manufactured medical device, for use in soluble solutions for treating a manufactured medical device, and so on. What is available is tubing, resins, and the like, having a hardness of 72A, 77A, 87A, 94A, 51 D, 60D, 63D, 67D, 73A/78A, 83A/86A, 90A/95A, 93A/98A, 55D/65D, 63D/78D, 73D, 75D/82D (Tecoflex® series); and 75A, 85A, 94A, 54D, 64D, 69D, 74D, 75D, 77A/83A, 87A/88A, 97A/97A, 55D/64D, 67D/75D, 70D, 75D, 77D/84D (Tecothane® series) (Lubrizol's Engineered Polymers for Medical and Health Care; Lubrizol Corp, Cleveland OH). Guidance on medical polymers, including polyurethane, is available, for example, from Polymer Membranes/Biomembranes (Advances in Polymer Science), ed. by Meier and Knoll, Springer, 2009; Lubricating Polymer Surfaces by Uyama, CRC Press, 1998; and Polymer Grafting and Crosslinking, ed. by Bhattacharya, et al, Wiley, 2008.

Reagents, including high purity solvents, as well as polymer resins such as 95A resin, can be acquired from Lubrizol Corp., Cleveland, OH; Microspec Corp., Peterborough, NH; Polaris Polymers, Avon Lake, OH; U.S. Plastic Corp., Lima, OH; Sigma-Aldrich, St. Louis, MO; E.I. du Pont de Nemours and Company, Wilmington, DE; Dow Chemical Co., Midland, MI. Polyurethane of durometer 95A is disclosed, for example, by US 2010/0082097 of Rosenblatt, et al, U.S. Pat. No. 6,517,548 issued to Lorentzen Cornelius, et al, and by U.S. Pat. No. 2011/0054581 of Desai and Reddy. Each of these is hereby incorporated herein by reference.

French Size

Diameters of catheters, cannulas, tubes, and such, can be labeled by French size. The disclosure provides a tube with a French size that is, to provide non-limiting examples, 3 Fr (1 mm; 0.039 inches), 4 Fr (1.35 mm; 0.053 inches), 5 Fr (1.67 mm; 0.066 inches), 6 Fr (2 mm; 0.079 inches), 7 Fr (2.3 mm; 0.092 inches), and so on. The corresponding diameters in millimeters and inches are shown in parenthesis. The French system has uniform increments between gauge sizes (⅓ of a millimeter) (Iserson K V (1987) J.-F.-B. Charrière: the man behind the "French" gauge. J. Emerg. Med. 5:545-548). Systems for measuring the outside diameter and inside diameter (lumen) of catheters, needles, and the like have been described (see, e.g., Ahn, et al. (2002) Anesth. Analg. 95:1125). French size can refer to an inside diameter or to an outside diameter (see, e.g., U.S. Pat. No. 7,641,645 issued to Schur, which is hereby incorporated by reference).

Block Copolymer Embodiments; Porosity Embodiments; Hydrogel Embodiments

Block copolymers are encompassed by the disclosure, for example, block copolymers of polyurethanes and block copolymers of polydimethylsiloxane (PDMS) with Polyurethanes (see, e.g., U.S. Pat. No. 8,008,407 of Oberhellman et al, and U.S. Pat. No. 8,084,535 of Maton et al, which are incorporated herein by reference in their entirety; and F. Wang, Polydimethylsiloxane Modification of Segmented Thermoplastic Polyurethanes and Polyureas, Thesis, Virginia Polytechnic Institute and State Univ., Blacksburg, VA, 1998). Regarding porosity, if the porosity of a polymer coating, impregnation, and such, is not sufficient to allow diffusion of alexidine into the extracellular fluids, a porosigen, such as lactose, hydrogels, or other release enhancement agents such as citric acid trisodium salt, polysorbate 80, or Tween 20®, and the like, can be added to the polymer used for the coating, impregnation, and such. Hydrogels, and methods for controlling water content of hydrogels, and mechanical strengths of various types of hydrogels are described (see, e.g., U.S. Pat. No. 4,734,097 of Tanabe et al, which is hereby incorporated by reference in its entirety). By way of definition, an example of "one type" of plastic polymer is, for example, a polymer that comprises mainly polyurethane, mainly polysiloxane, mainly polyethylene, or mainly one type of copolymer. The skilled artisan will understand that modification of a polyurethane polymer with various end groups do not change the fact that the polymer is still classified as a "polyurethane." A "copolymer" is defined as consisting mainly of "one type" of plastic polymer, because the two polymers in the copolymer are integrated together, and are also covalently bound to each other, for example, in the manner of a block copolymer of polycarbonate polyurethane, e.g. Carbothane® or Quadrathane®.

Stabilizers and Hydrogels

The devices, catheters, tubular members, solvents, coatings, impregnations, treatments, and related methods, can encompass stabilizers such as citrate. What is encompassed is one or more stabilizers that reduce discoloration, that reduce cracking or flaking, that reduce formation of a "shark skin" surface, that reduce oxidation, or that reduce other aspects of aging and storage. What is also encompassed is a coating (or impregnation, or combination of coating and impregnation, or bulk-distribution) that includes a hydrogel, for use in improving the release profile, or for extending the efficacy of the alexidine, or for modulating the release profile of the alexidine, e.g., to make release more uniform over the course of weeks, months, or years. Hydrogels, and methods for characterizing hydrogels, have been described (see, e.g., Qiu and Park (2001) Adv. Drug Delivery Reviews. 53:321-339; Bromberg and Ron (1998) Adv. Drug Delivery Reviews. 31:197-221; Wei et al (2009) Biomaterials. 30:2606-2613; Westhaus and Messersmith (2001) Biomaterials. 22:453-462; Sosnik and Cohn (2004) Biomaterials. 25:2851-2858; Kim et al (2009) Biomacromolecules. 10:2476-2481).

Anti-Biofouling Treatments

The present disclosure provides, without limitation, coatings or other treatments, such as sulfobetaine, carboxybetaine, polymer hydrogels such as a crosslinked polysulfobetaine hydrogel, carboxybetaine acrylates, carboxybetaine acrylamides, carboxybetaine vinyl compounds, carboxybetaine epoxides, sulfobetaine acrylates, sulfobetaine acrylamides, sulfobetaine vinyl compounds, sulfobetaine epoxides, sulfobetaine methacrylate (SBMA), polyurethane, polyester, polyethylene, polyamide, mixtures thereof, diblock polymers, layered coatings, layered treatments, interpenetrating polymer networks, (see, e.g., U.S. Pat. No. 7,879,444 issued to Jiang et al; US 2009/0259015 of Jiang and Chen; US 2009/0155335 of O'Shaughnessey et al; US 2009/0156460 of Jiang et al; US 2010/0145286 of Zhang et al; 2011/0097277 of Jiang et al; and US 2010/0152708 of Li et al, each of which is individually incorporated herein by reference in its entirety.

Structures of Catheters Configured for Various Organ Systems

The present disclosure provides catheter that are specifically configured, in terms of shape, size, and composition, for use in various organ systems, for example, as a cardiovascular catheter, urinary tract catheter, colorectal catheter, or pulmonary tract catheter. Guidance for specific shapes, dimensions, size, and chemical composition are available. See, for example, Mort (2007) Critical Care and Trauma. 105:1357-1362; Taylor et al (2003) Radiology. 229:99-108; Akahoshi et al (2001) Brit. J. Radiology. 74:1017-1022; Walter et al (2009) J. Spinal Cord Med. 32:578-582; Mohammed et al (2008) Expert Rev. Med. Devices. 5:705-707; Durst et al (2007) Imaging and Diagnostic Methods. 9:290-293; AARC Clinical Practice Guidelines (2010) Respir. Care. 55:758-764; Thomas et al (2011) J. Invasive Cardiol. 23:536-539; Besarab et al (2011) Clin. J. Am. Soc. Nephrol. 6:227-234; Knuttinen et al (2009) Seminars in Interventional Radiology. 26:106-114; Royle et al (2008)

Ann. R. Coll. Surg. Engl. 90:679-684. The present disclosure provides specific catheters, methods of manufacture, and method of use, specifically configured for organs, vessels, and lumens, of the eye, ear, spinal column, trachea, nose, trachea, lungs, artery, vein, heart, colon, rectum, male or female reproductive tract, foetus, urinary tract, kidney, pancreas, any anastomosing vascular region, esophagus, stomach, duodenum, ileum, jejunum, interstitial spaces, bone marrow, tumor vasculature, and so on.

The present disclosure provides formulations, as well as medical devices treated with or impregnated with, the formulations of the present disclosure. Catheters and other medical devices, treated or impregnated with an antimicrobial agent, and configured for use in different regions of the body, are provided. These include, for example, vascular catheters, epidural catheters, endotracheal tubes, and urinary catheters. Nanocomposites, membranes, films, sandwiches, tubes, and the like, are encompassed by the present disclosure (see, e.g., Fong, et al. (2010) Acta. Biomater. 6:2554-2556; Huynh, et al (2010) Eur. J. Pharm. Biopharm. 74:255-264; Berra, et al (2008) Intensive Care Med. 34:1020-1029).

Exclusionary Embodiments

What can be excluded, is a device, system, method of using, or method of manufacturing, that encompasses triclosan. What can be excluded, is a device, system, method of using, or method of manufacturing, that encompasses a metal compound. What can be excluded, is a device, system, method of using, or method of manufacturing, that encompasses silver. What can be excluded, is a device, system, method of using, or method of manufacturing, that encompasses one or more of a Lewis acid, triarylmethane dye, methyl violet, brilliant green, gentian violet, and the like. Moreover, what can be excluded, is a device, system, method of using, or method of manufacturing, that encompasses an inhibitory polymer, such as one or more of a hydrophilic inhibitory polymer, a hydrophobic inhibitory polymer, polyethylene glycol, polyethylene oxide, polyvinylpyrrolidone, polyvinyl alcohol, polytetrafluoroethylene, hexafluoropropene, polyvinylidine, difluoride, fluorinated ethylene propylene, and the like. Furthermore, what can be excluded is a device, system, method of using, or method of manufacturing, where an antimicrobial agent and an inhibitory polymer are separate, for example, by residing in two different layers, residing in two different layers and separated from each other by a third layer. Separation can also be by residence into two different regions of a device, for example, at a distal end versus at a proximal end, or in a dilator versus in a sheath.

In exclusionary embodiments, what is encompassed by the present disclosure is a medical device that does not comprise chlorhexidine. In this embodiment, what is excluded are all medical devices that comprise chlorhexidine. Also what is encompassed is a medical device that does not comprise triclosan, does not comprise a silver salt, does not comprise the combination of triclosan and silver salt, does not comprise zinc, does not comprise sulfadiazine, does not comprise chlorhexidine, does not comprise panthenol, octoxyglycerin, phenoxyethanol, iodine compound, or parachlorometaxylenol, or does not comprise octoxyglycerin, miconazole, or the combination of octoxyglycerin and miconazole, does not comprise an anti-microbial agent that is other than alexidine, or does not comprise an anti-thrombogenic agent other than alexidine. Without implying any limitation to the present disclosure, device exclusionary embodiments can exclude a device coated with, impregnated with, or treated with, zinc acetate, zinc lactate, a water-soluble zinc salt, panthenol, octoxyglycerin, phenoxyethanol, iodine compound, parachlorometaxylenol, octoxyglycerin, miconazole, combination of oxtoxyglycerin and miconazole, or any exclusionary combination of the above.

In exclusionary embodiments, the present disclosure can exclude any device where an antimicrobial agent is bulk distributed, can exclude any device where an antimicrobial agent occurs substantially in an extrusion coating, can exclude any device where an antimicrobial agent occurs substantially with an impregnation (rather than with a coating), and can exclude any device where an antimicrobial agent occurs substantially as a coating (rather than as an impregnation).

What can also be excluded is any medical device comprising an anti-inflammatory agent, or any medical device that has a coating (or impregnation, or both coating and impregnation) that comprises an anti-inflammatory agent, e.g., salicylic acid.

In exclusionary embodiments, what is provided is a formulation for treatment, or a treated medical device, where the only polymer used in treating is Tecoflex®, Texothane®, Texin®, Carbothane®, Quadrathane®, Elast-Eon®, Estane®, or Pellethane®. The skilled artisan can readily determine the chemical structure of polymer compositions identified by trade names. For example, what is provided is a formulation that does not include Pellethane. In other exclusionary embodiments, what is provided is a formulation for treatment, or a treated medical device, where the only polymer in the treatment is Tecoflex®, Texothane®, Texin®, Carbothane®, Estane®, or Pellethane®. For example, what is provided is a formulation that does not include Pellethane.

The skilled artisan will understand that use of an agent to reduce growth of bacteria, fungi, or other microbes on a medical device does not constitute a method of medical treatment. The skilled artisan will also understand that anti-thrombogenic agent of the present disclosure concerns an interaction between a medical device and one or more enzymes or proteins, and that this is not a method of medical treatment.

The concentration can also be measured in situ, for example, with a technique involving fluorescence, radioactivity, or microbiological assays. Catheter is a non-limiting example. A microbiological assay configured for measuring the concentration of the amount of antimicrobial within a catheter can be measured as follows. A series of catheters, pre-impregnated with various concentrations of known antimicrobial, can be inoculated with the same quantity of a bacterium. The inoculated catheter can then be incubated under conditions suitable for growth of the bacteria, for example, including nutrients and a temperature of 37 degrees C. Following an incubation time of, for example, 1-7 days, the quantity of bacterial can then be measured. The amount of impregnated antimicrobial can be expressed in terms of a unit of percent maximal efficacy, or the amount of impregnated antimicrobial can be expressed with reference to a standard catheter containing a known quantity of antimicrobial. Methods are available for converting any organic molecule into a corresponding radioactive molecule that contains tritium (see, e.g., Saljoughian and Williams (2000) Curr. Pharm. Des. 6:1029-1056). Where a molecule is tritiated, it residence, diffusion, and migration, can easily be monitored.

The present disclosure provides a formula that, when coated, impregnated, treated, or soaked, into a medical device, and when tested in the above microbiological assay, results in less than 80% maximal number of bacteria, less than 60%, less than 40%, less than 20%, less than 10%, less than 10%, less than 5%, less than 1%, less than 0.1%, less than 0.01%, less than 0.001%, less than 0.0001%, maximal number of bacteria. Maximal number of bacteria is measured with a control medical device, where the control medical device had been treated with solvents only (but not with any antimicrobial agent). Biofilm measurements can also be used to assess efficacy of the compositions, devices, and methods of the present disclosure. Biofilm can be measured (see, e.g., Peeters et al (2008) J. Microbiol. Methods. 72:157-165; Bakke et al (2001) J. Microbiol. Methods. 44:13-26). The present disclosure reduces biofilm to less than 80%, less than 60%, less than 40%, less than 20%, less than 10%, less than 5%, less than 1%, less than 0.1%, and so on, when compared to control value.

In some embodiments of the microbiological assay, the culturing medium is a complete nutrient medium that allows growth of the test organism. In other embodiments, the culturing medium is an incomplete nutrient medium that allows maintenance of the test organism, but does not support growth.

Measuring Biological Efficacy of an Agent that Resides in or on a Medical Device, without Extracting the Agent from the Medical Device Anti-microbial efficacy of the medical device can be assessed by inoculating the medical device with a microbe, and by monitoring the ability of the anti-microbial agent to reduce growth, to reduce attachment, or to kill, the microbe, or to impair formation of a biofilm. Anti-microbial activities taking place on the surface of the medical device, or within the matrix or pores of the medical device, can be assessed by light microscopy or electron microscopy, using methods well known to the skilled artisan. A medical device containing an anti-microbially effective amount of an anti-microbial agent can be measured by detecting the number of microorganisms that colonize the surface of a medical device or that colonize pores or a matrix of a medical device. Alternatively, and without limitation, anti-microbially effective can be measured by incubating the medical device in a liquid medium, or an agar medium, and by detecting the number of microorganisms that colonize the surface of medical device, or that colonize a pre-determined area or volume apart from the surface of the medical device, for example, an area that is 0 mm to 1 mm away from the surface of the medical device, that is 1 mm to 3 mm away, from 0 mm to 3 mm away, 2 mm to 5 mm away, from 0 mm to 5 mm away, from 2 mm to 20 mm away, and the like. Control medical devices can be treated with sham formulation only (no anti-microbial) or can be treated with an active control.

Methods and equipment are available to the skilled artisan for measuring structures, properties, and functions, of medical devices, such as catheters. The following references disclose methods and equipment for measuring, for example, tensile strength, force at break, elastic behavior, plastic behavior, microscopy for detecting microbial colonies or biofilms residing on the surface of catheters, microbiological assays for measuring influence of anti-microbials. See, e.g., Aslam and Darouiche (2010) Infect. Control Hosp. Epidemiol. 31:1124-1129; Hachem et al (2009) Antimicrobial Agents Chemotherapy 53:5145-5149; Venkatesh et al (2009) J. Medical Microbiol. 58:936-944, which are hereby incorporated herein by reference. Methods and equipment for measuring tensile strength, elongation at break, and other properties of medical devices, are available. See, e.g., U.S. Pat. No. 6,039,755 issued to Edwin et al, and U.S. Pat. No. 7,803,395 issued to Datta et al, which are incorporated herein by reference. Above a limiting stress, called the elastic limit, some of the strain is permanent. In going beyond the elastic limit, a solid can either fracture suddenly or deform in a permanent way (see, e.g., Ashby M F, Jones D R H (2012) Engineering Materials 1, 4$^{th}$ ed., Elsevier, New York, pp. 115-133).

Blood Clotting Assays

Influence of alexidine on blood clotting can be measured by a number of assay methods. Clotting time can be measured by the Quick method, by the Owren method (Schnick et al (2009) Critical Care. 13:R191 (15 pages); Osman et al (2009) Scand. J. Clin. Lab. Invest. 69:395-400). The Owren method measures only coagulation factors II, VII, and X, because fibrinogen and factor V are in the reagent. Prothombin Time (PT) measures the extrinsic (tissue factor) pathway of coagulation, and is a standard test for monitoring efficacy of oral anticoagulation therapy. Activate Clotting Time (ACT) can be assessed by instruments, which are available, e.g., from Helena Laboratories (Beaumont, TX); ITC (Edison, NJ); Medtronics (Minneapolis, MN), and Roche Diagnostics (Indianapolis, IN). Thrombin clotting time (TCT) measures the thrombin-induced conversion of fibrinogen to fibrin, bypassing all other blood clotting factors. TCT can be performed by adding thrombin to citrated plasma, and measuring the time required for the formation of fibrin monomers (see, e.g., Jespersen and Sidelmann (1982) Acta Haematol. 67:2-7).

Platelet aggregation can be measured using instruments and reagents from, for example, Chrono-Log Corp., Havertown, PA; Bio/Data Corp., Horsham, PA; Helena Laboratories, Beaumont, TX; Medtronic, Minneapolis, MN). ACT uses tubes containing an activator, such as kolin or celite. Tests for enzymatic activities of individual clotting factors can be conducted using chromogenic substrates, for example, substrates for thrombin, tissue-type plasminogen activator, urokinase, factor IX, factor X, and factor XII. Instruments are available for measuring prothrombin times, activated partial thromboplastin times (APTT), fibrinogen concentrations (Clauss test) (see, e.g., KC4® Coagulation Analyzer, Sigma Amelung, Lemgo, Germany).

As measured by any of the above methods, alexidine impairs blood clotting, or one or more steps in the blood clotting cascade, to a greater extent than another agent, for example, an agent that is chlorhexidine. Where an agent impairs blood clotting, as compared to another agent, the impairment can be measured in terms of an increase in blood clotting time, e.g., an increase that is at least 1.5-fold, at least 2.0-fold, at least 4-fold, at least 5-fold, at least 10-fold, at least 20-fold, at least 40-fold, at least 50-fold, in terms of time. Also, where an agent impairs blood clotting, the impairment can be measured in terms of a reduction in clot size, e.g., where the clot is less than 90% maximal, less than 80% maximal, less than 50% maximal, less than 25% maximal, less than 10% maximal, and the like, at a given time. Also, where an agent impairs blood clotting, the impairment can be measured in terms of inhibited enzymatic activity of a blood clotting factor, for example, where the inhibited blood clotting factor's activity is less than 90% maximal, less than 80% maximal, less than 50% maximal, less than 25% maximal, less than 10% maximal, and the like, at a given time.

Where clotting time is measured by comparing a medical device that is treated with alexidine, with a medical device that is not treated with alexidine, the results of the measurement can be used to assess the efficacy of the medical device in preventing pathological blood clots. However, difficulty in assessing the true efficacy of the medical device may result where the medical device is treated with alexidine plus a second agent that prevents blood clotting. The second agent may have the advantage, for example, of reducing the needed concentration of alexidine, of having a more prolonged residence in the resulting coating or impregnation than alexidine, and so on. The difficulty is that the second agent may conceal the efficacy of alexidine. In this case, the efficacy of the alexidine-coated medical device is preferably assessed by using a medical device that is coated with alexidine, but where the second agent is omitted during the treatment.

In embodiments, the present disclosure provides methods, reagents, treated medical devices, coated medical devices, impregnated medical devices, and the like, where use of alexidine has an anti-thrombogenic effect, where alexidine has an anti-clotting effect, where alexidine has an anti-blood coagulation effect, and so on. In embodiments, alexidine inhibits clotting, resulting in less than 90% clotting, as compared to a control, less than 80%, less than 70%, less than 60%, less than 50%, less than 40%, less than 30%, less than 20%, less than 10%, less than 5%, as compared to a control. In embodiments, alexidine's inhibition of clotting results in a prolongation of clotting time by at least 20%, at least 50%, at least 100% (2-fold), at least 3-fold, at least 4-fold, at least 5-fold, at least 10-fold, at least 20-fold, and the like, when compared to a control. A suitable control is the same method, reagent, treated, coated, or impregnated medical device, where no anti-microbial agent is used. Another suitable control, is where chlorhexidine is used in place of alexidine.

Chemical and Microbiological Assay Methods for Alexidine

Alexidine can be measured by HPLC (high pressure liquid chromatography; high performance liquid chromatography) using a reverse phase LC column (Agilent, Santa Clara, CA). Detection can be performed at 210 nm wavenumber with a UV detector. Alexidine can also be measured with Liquid Chromatography-Mass Spectroscopy (LCMS) or with Fourier Transform Infrared (FTIR) Spectroscopy. What can be measured is alexidine extracted from a medical device, or alexidine samples prior to soaking or treating a medical device. Alexidine can also be measured by way of microbiological assays, for example, assays where circular filter papers impregnated with various known concentrations of alexidine, or with an unknown sample of alexidine, are placed on a seeded lawn of bacteria on nutrient agar. This type of microbiological assay results in a zone of inhibition, where a larger diameter zone indicates a greater amount of alexidine.

DETAILED DESCRIPTIONS OF THE FIGURES

FIG. 1 discloses microbial colonization reduction that demonstrates broad spectrum antimicrobial efficacy of alexidine-treated peripherally inserted central catheters (PICCs). Each of the histogram bars represents the $\log_{10}$ reduction, in surface colonization by the test microbe, as compared to the initial inoculum. Table 4 discloses the number of microbial cells (bacterial cells or fungal cells) in the initial inoculum, and the $\log_{10}$ reduction in the biomass adherent to the catheter surface as compared to the initial inoculum. The steps in the experiment involved first, soaking catheters in (+/−) alexidine, incubating in human plasma for the number of days indicated in the FIG. 1, followed by inoculation with the indicated microbe and a 1-day incubation to allow microbial growth. The results in FIG. 1 demonstrate that prolonged incubation in the human plasma did not result in any progressive losses in anti-microbial activity.

Figure 2A:
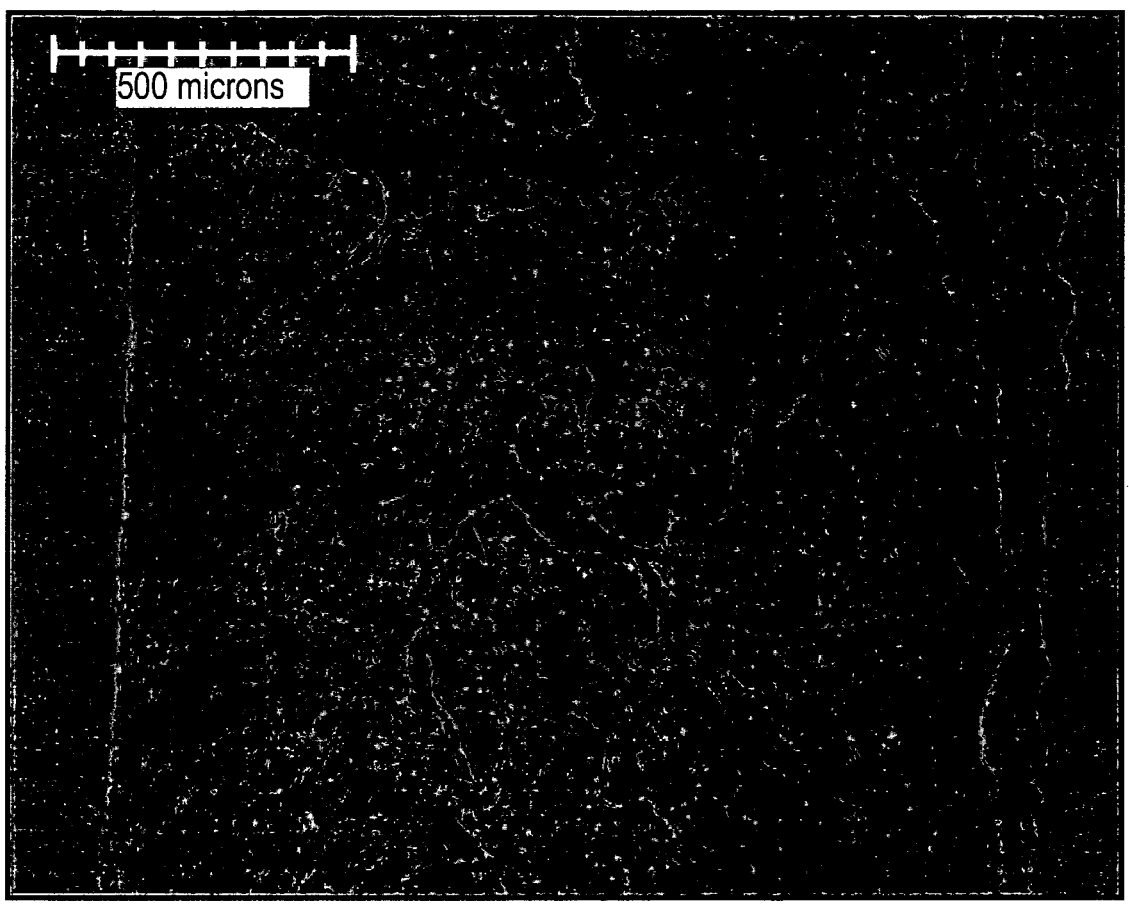
FIG. 2A and FIG. 2B disclose 70× magnification scanning electron microscopy (SEM) photographs of an untreated catheter.
Figure 2B:
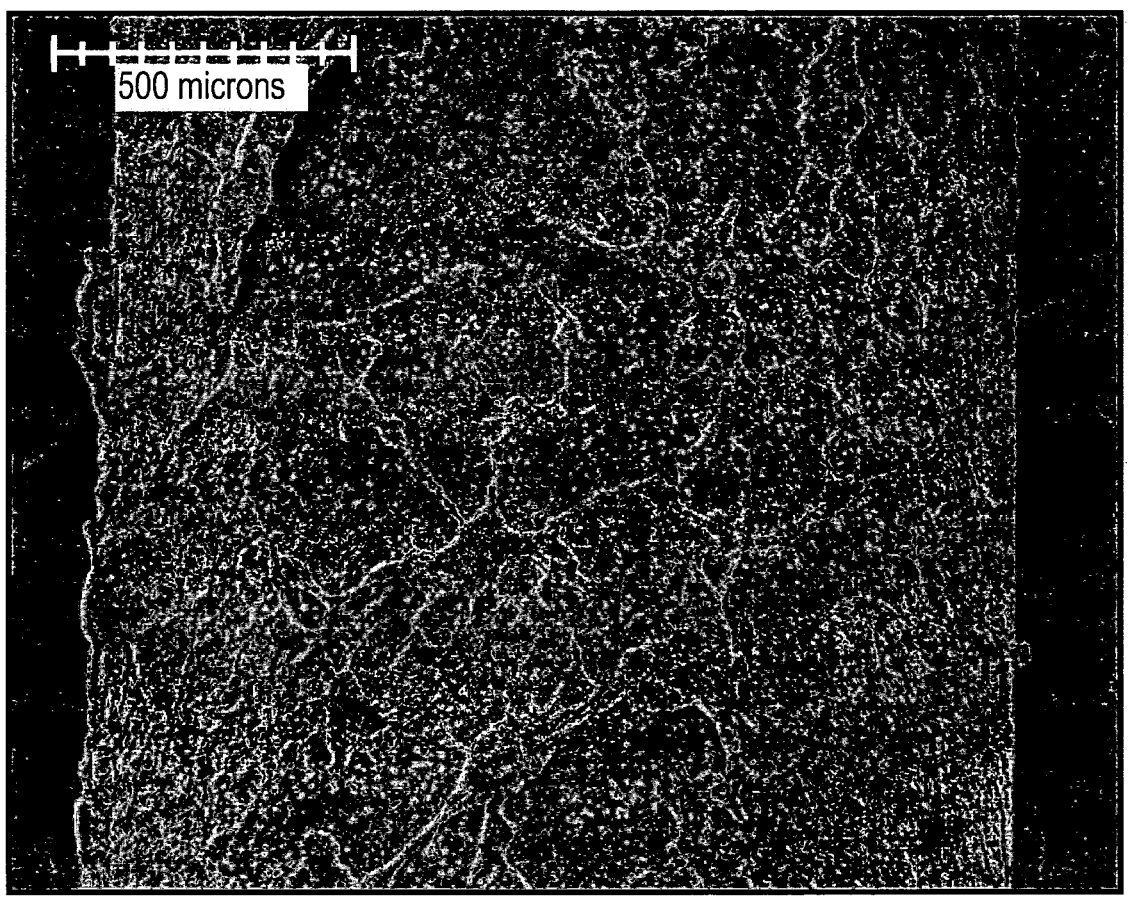

FIG. 2A and FIG. 2B disclose 70× magnification scanning electron microscopy (SEM) photographs of an untreated catheter. The bar at the top left shows a length of 500 micrometers (0.5 mm).

Figure 3A:
FIG. 3A and FIG. 3B show 500× magnification SEM photographs of untreated catheter.
Figure 3B:
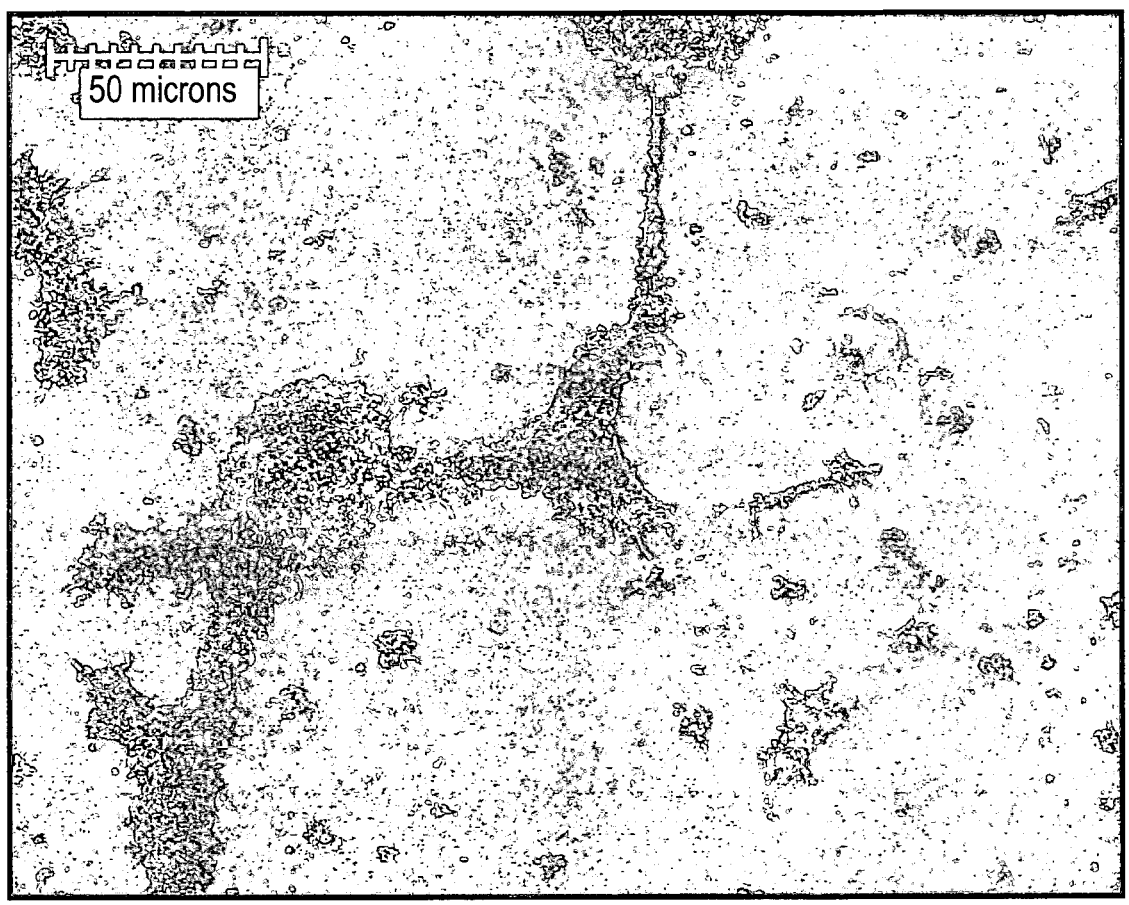

FIGS. 3A and 3B show 500× magnification SEM photographs of untreated catheter. The bar at the top left shows a length of 50 micrometers.

Figure 4A:
FIG. 4A and FIG. 4B show 2000× magnification SEM photographs of untreated catheter.
Figure 4B:

FIGS. 4A and 4B show 2000× magnification SEM photographs of untreated catheter. The bar at the top left shows a length of 10 micrometers.

Figure 5A:
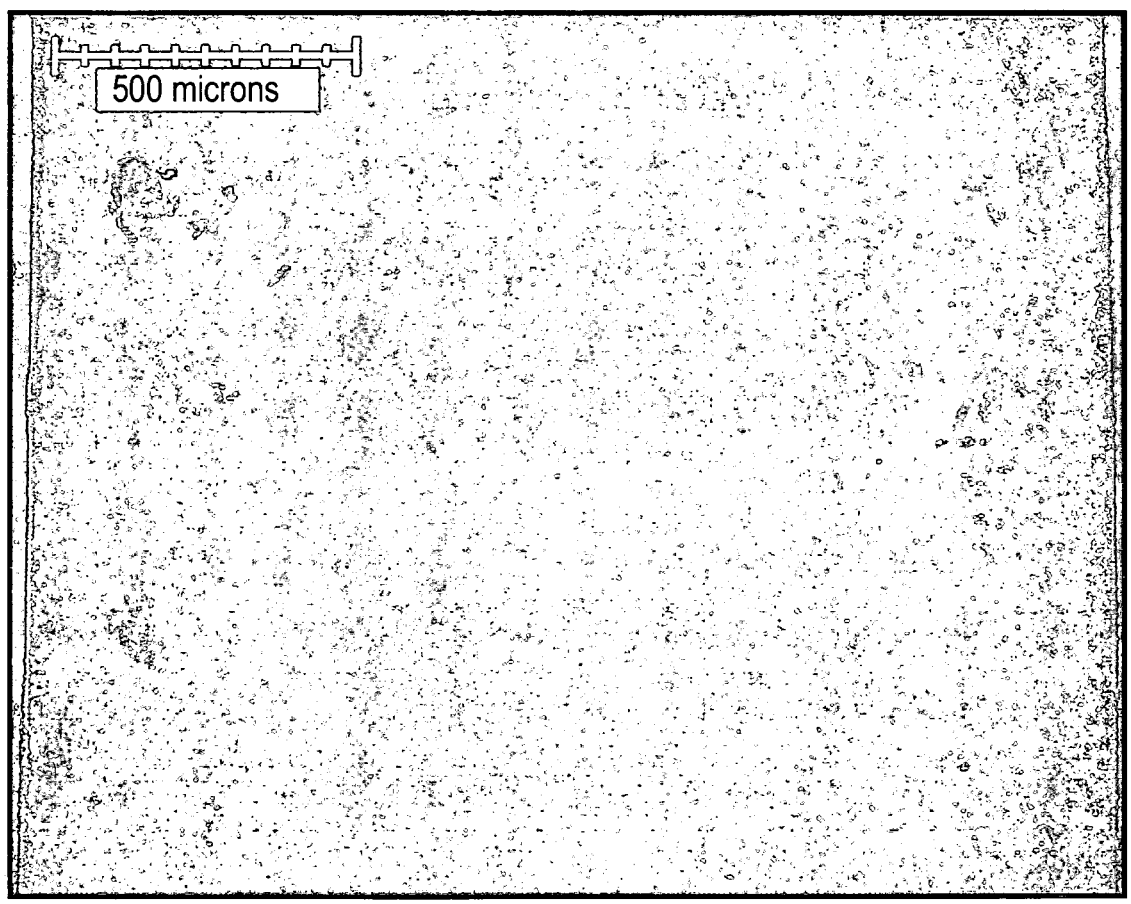
FIG. 5A and FIG. 5B disclose 70× magnification scanning electron microscopy (SEM) photographs of chlorhexidine-treated catheter.
Figure 5B:
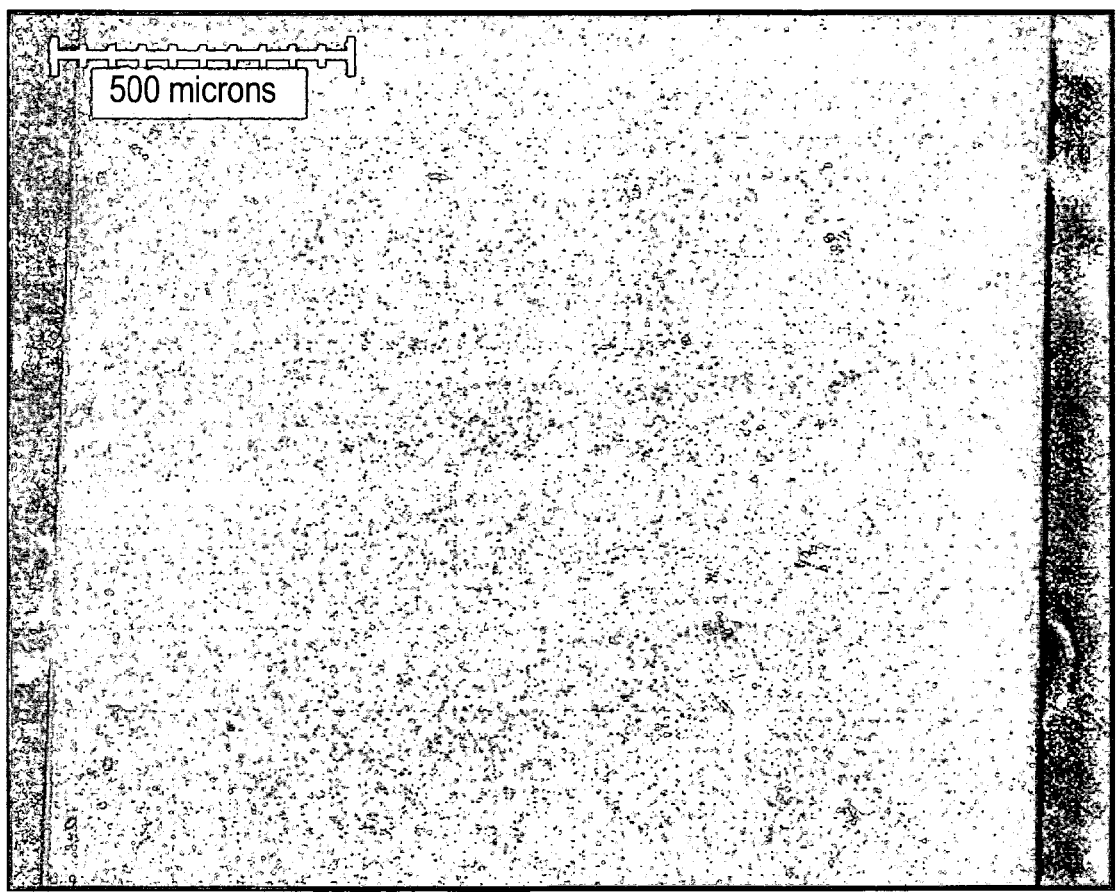

FIG. 5A and FIG. 5B disclose 70× magnification scanning electron microscopy (SEM) photographs of chlorhexidine-treated catheter. The bar at the top left shows a length of 500 micrometers (0.5 mm).

Figure 6A:
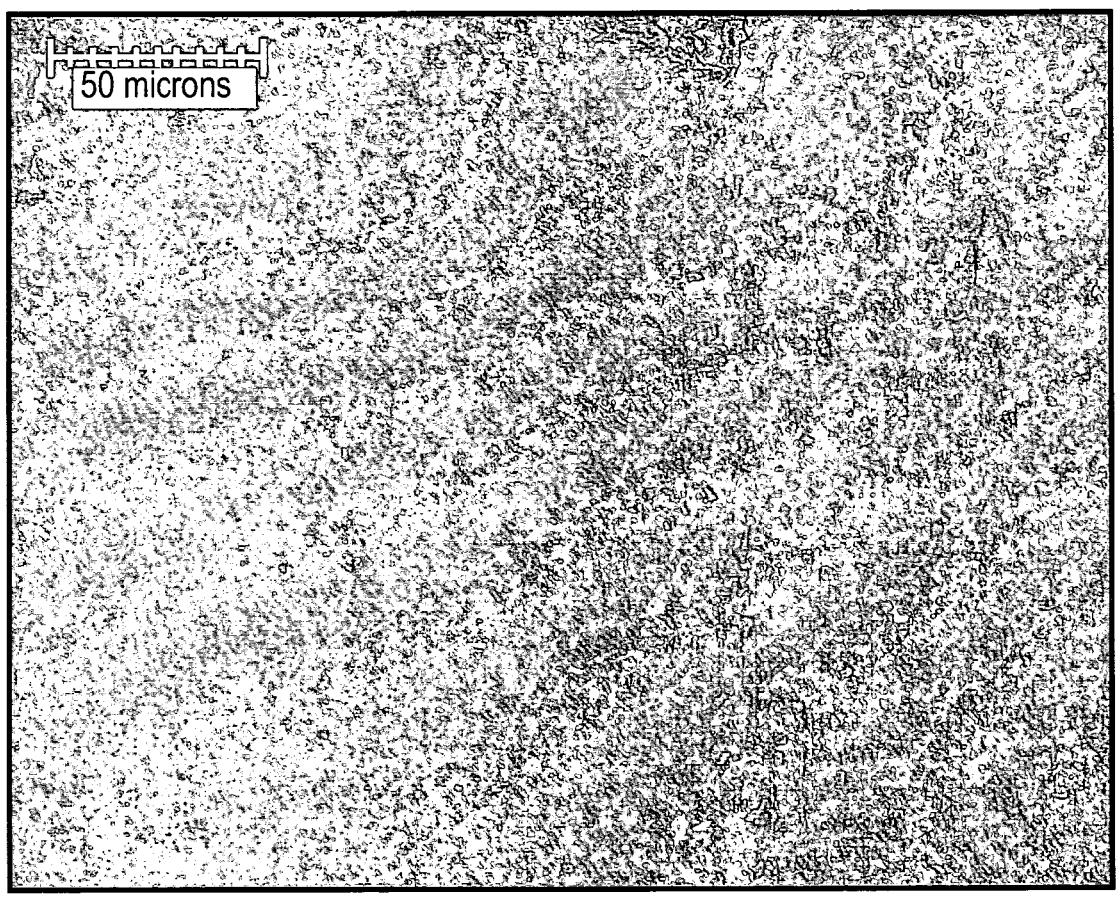
FIG. 6A and FIG. 6B disclose 500× magnification scanning electron microscopy (SEM) photographs of chlorhexidine-treated catheter.
Figure 6B:
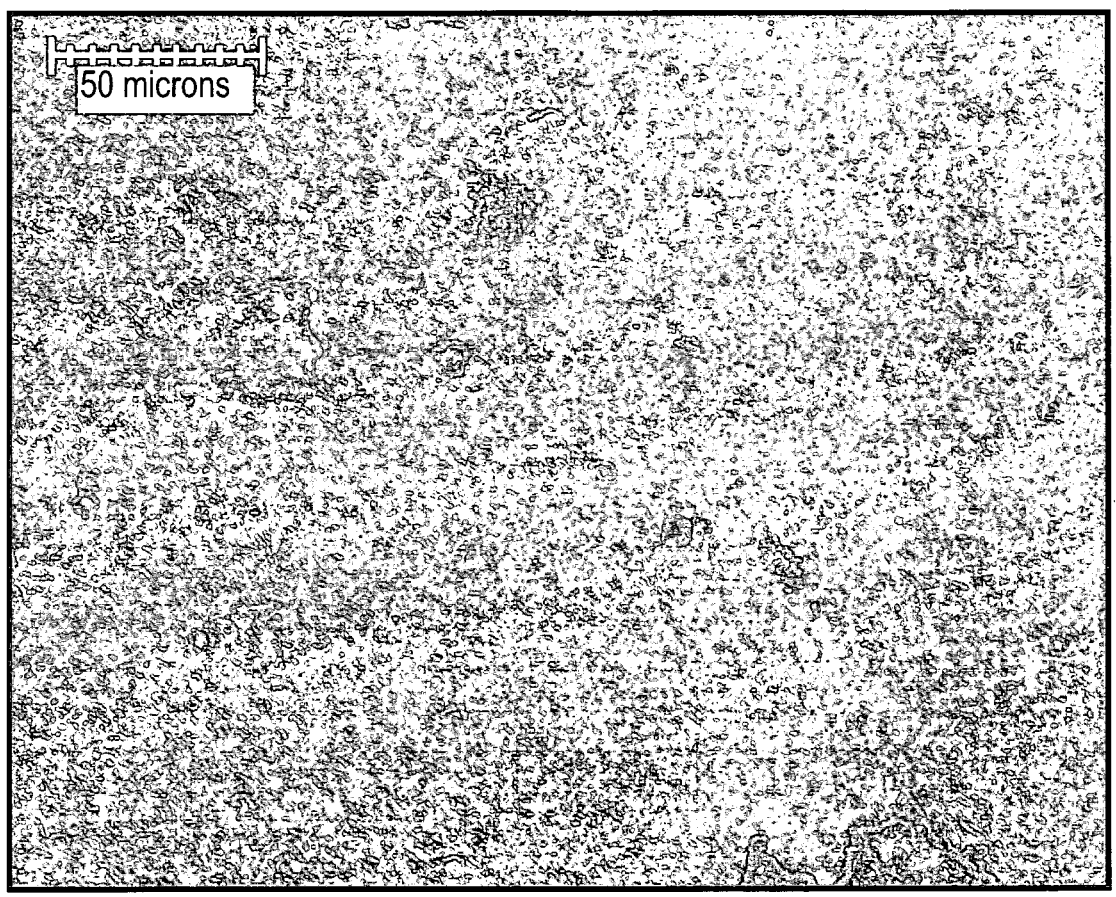

FIG. 6A and FIG. 6B disclose 500× magnification scanning electron microscopy (SEM) photographs of chlorhexidine-treated catheter. The bar at the top left shows a length of 50 micrometers.

Figure 7A:
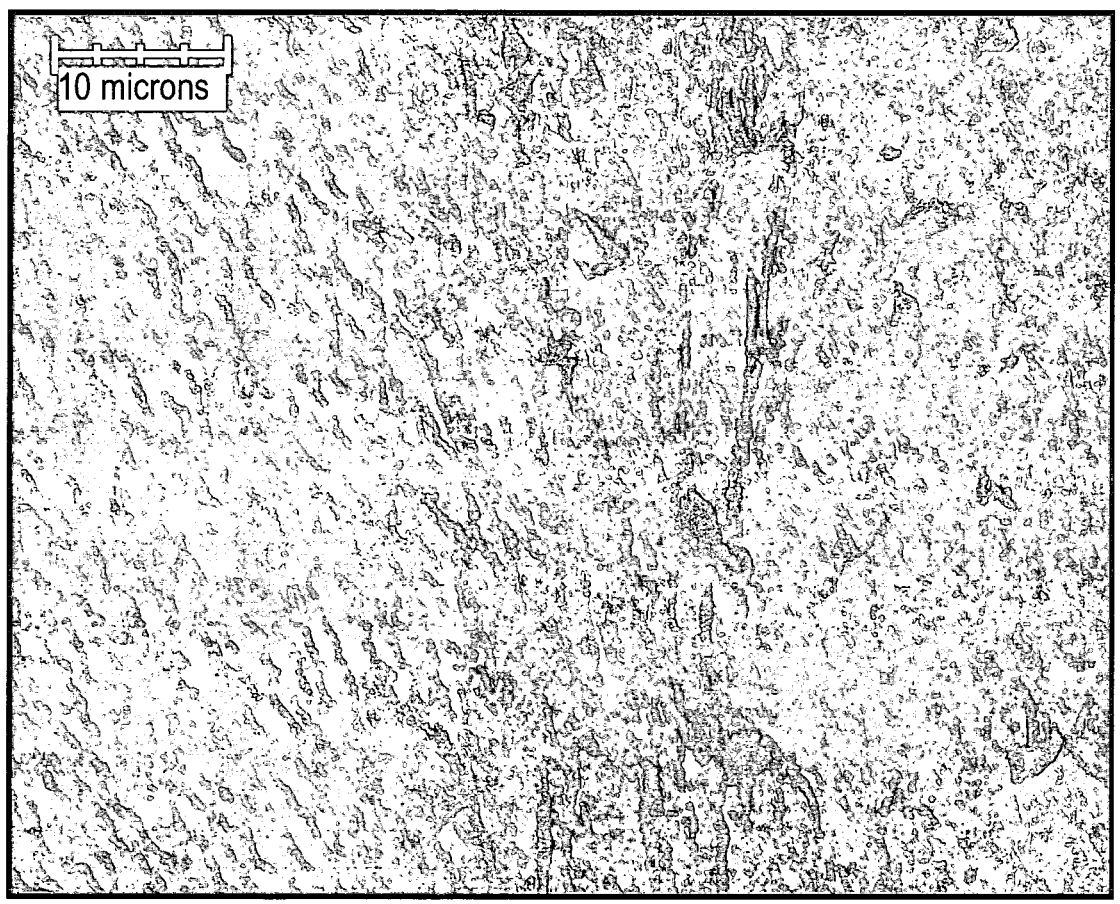
FIG. 7A and FIG. 7B disclose 2000× magnification scanning electron microscopy (SEM) photographs of chlorhexidine-treated catheter.
Figure 7B:
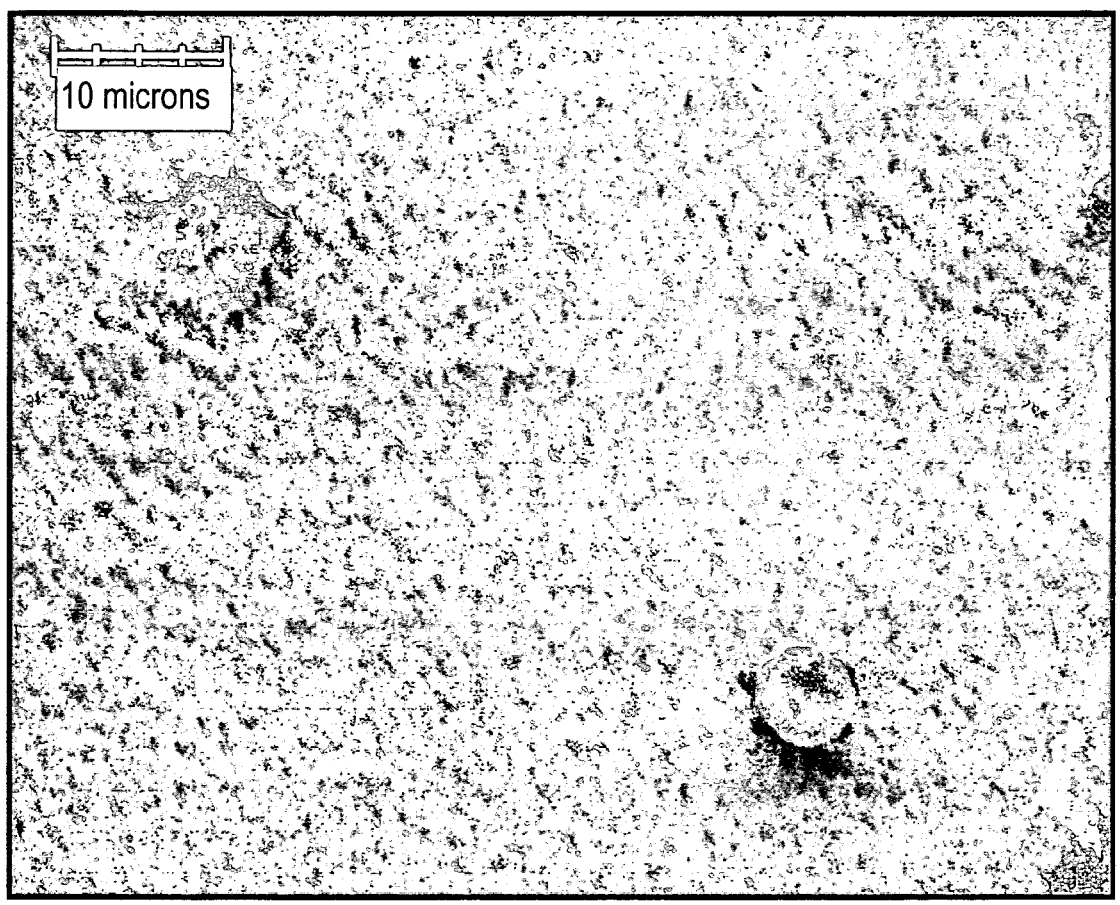

FIG. 7A and FIG. 7B disclose 2000× magnification scanning electron microscopy (SEM) photographs of chlorhexidine-treated catheter. The bar at the top left shows a length of 10 micrometers.

Figure 8A:
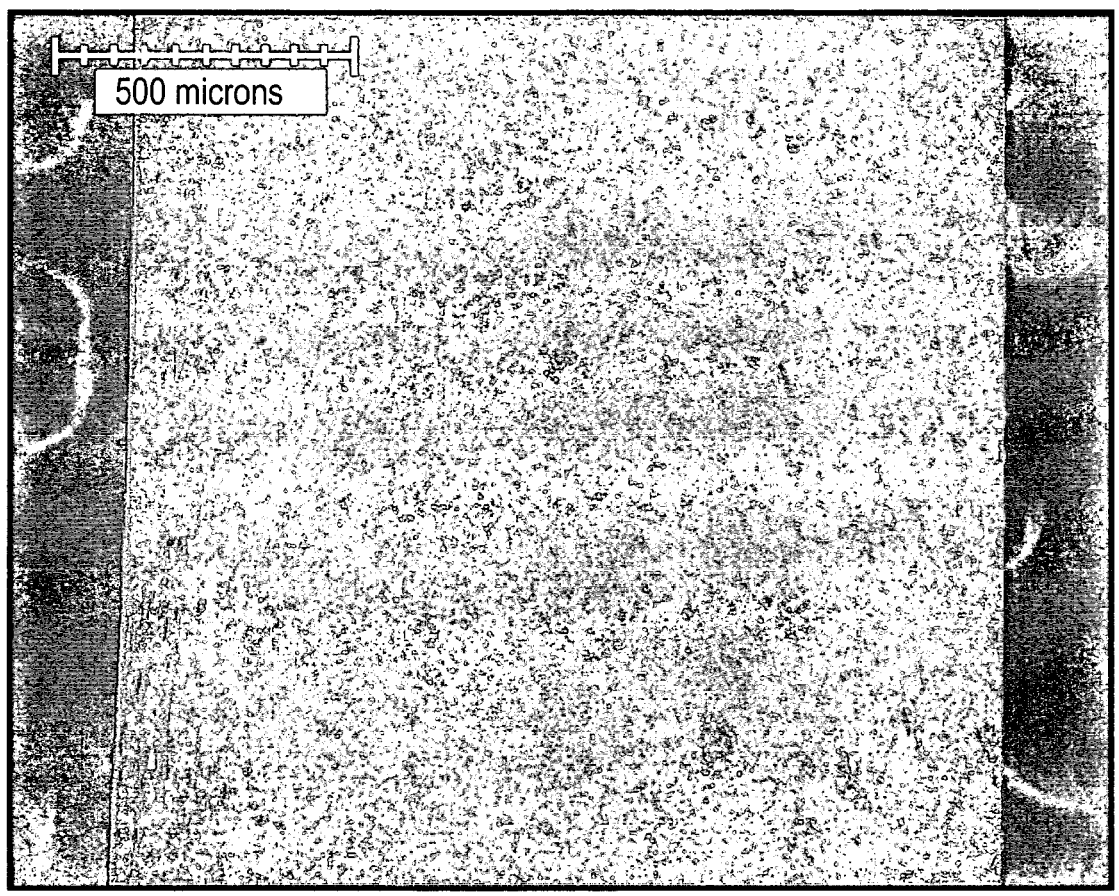
FIG. 8A and FIG. 8B disclose 70× magnification scanning electron microscopy (SEM) photographs of alexidine-treated catheter.
Figure 8B:
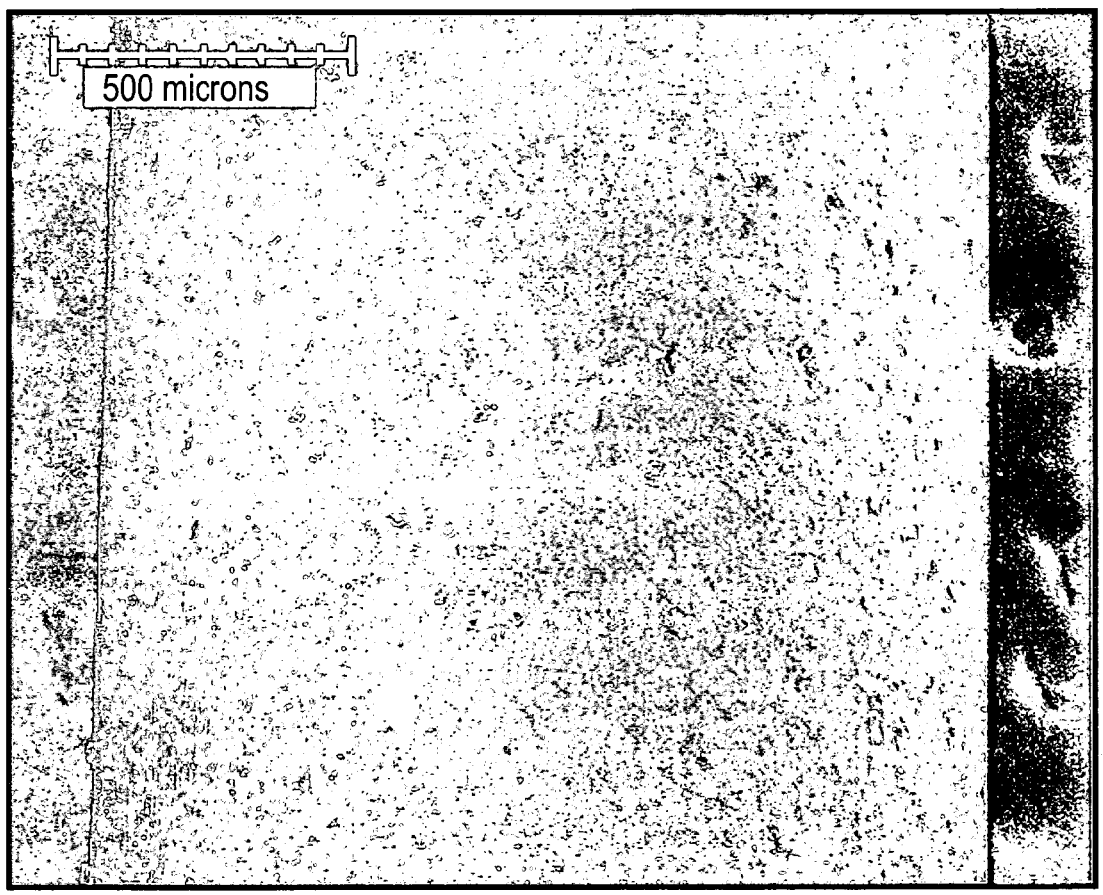

FIG. 8A and FIG. 8B disclose 70× magnification scanning electron microscopy (SEM) photographs of alexidine-treated catheter. The bar at the top left shows a length of 500 micrometers (0.5 mm).

Figure 9A:
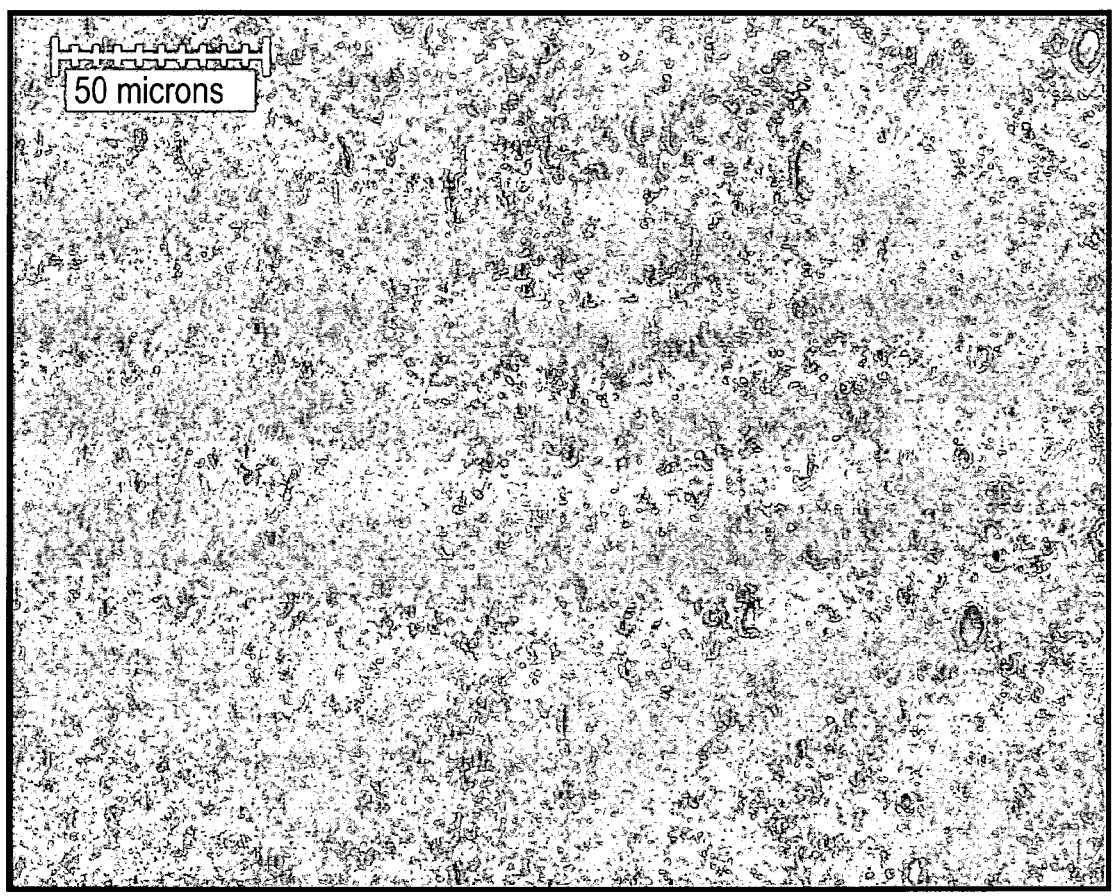
FIG. 9A and FIG. 9B disclose 500× magnification scanning electron microscopy (SEM) photographs of alexidine-treated catheter.
Figure 9B:
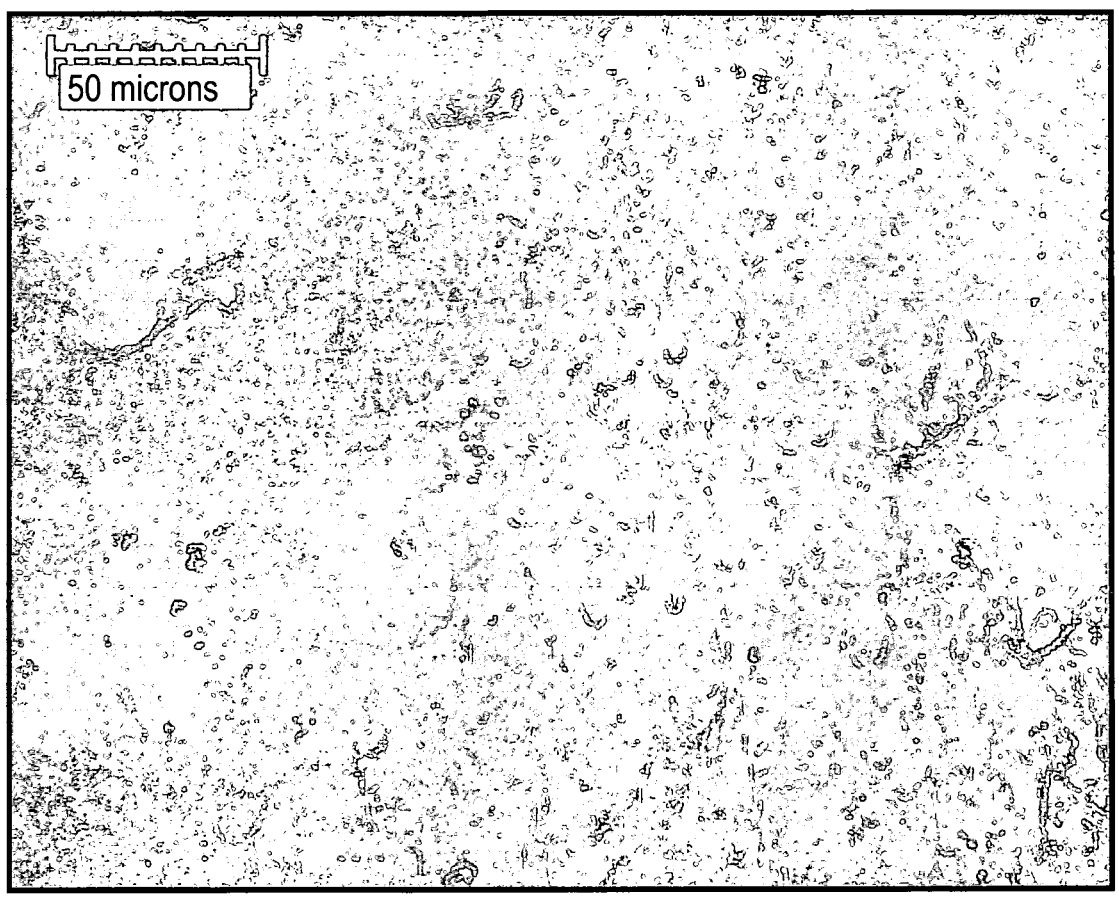

FIG. 9A and FIG. 9B disclose 500× magnification scanning electron microscopy (SEM) photographs of alexidine-treated catheter. The bar at the top left shows a length of 50 micrometers.

Figure 10A:
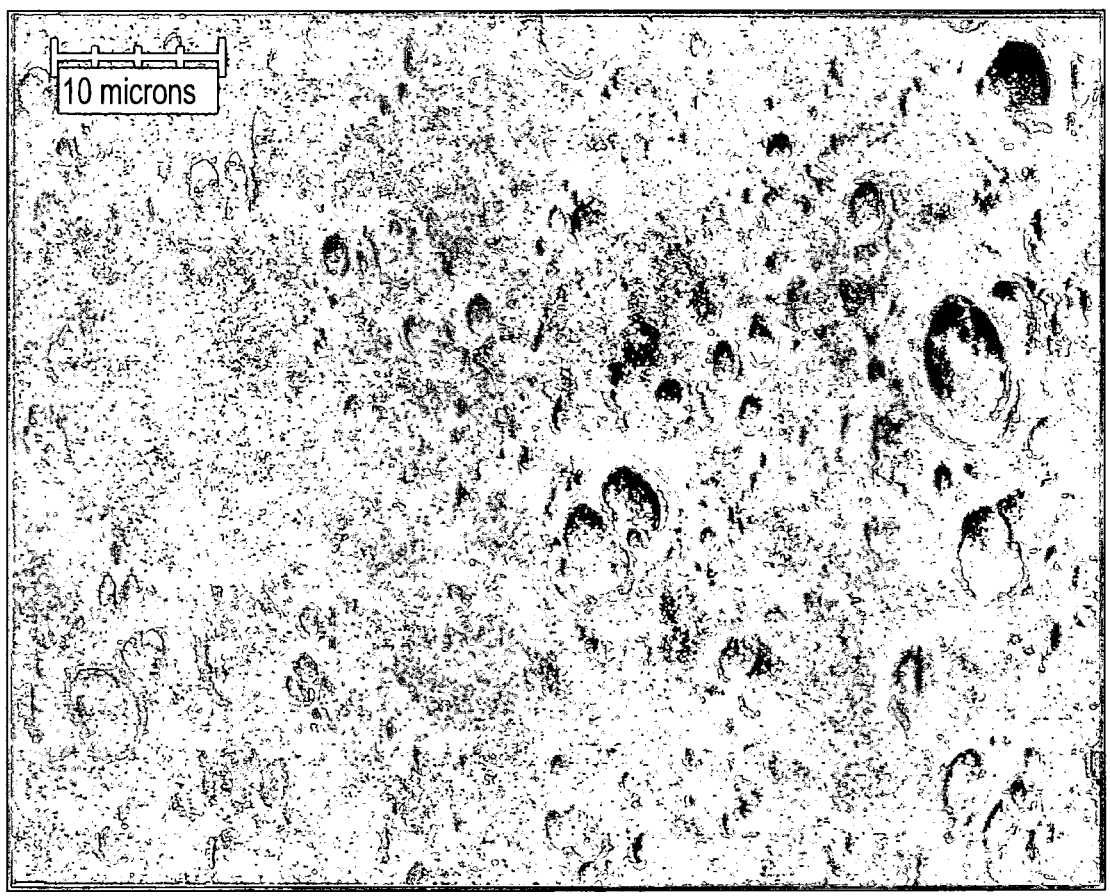
FIG. 10A and FIG. 10B disclose 2000× magnification scanning electron microscopy (SEM) photographs of alexidine-treated catheter.
Figure 10B:

FIG. 10A and FIG. 10B disclose 2000× magnification scanning electron microscopy (SEM) photographs of alexidine-treated catheter. The bar shows a length of 10 micrometers.

Figure 11:
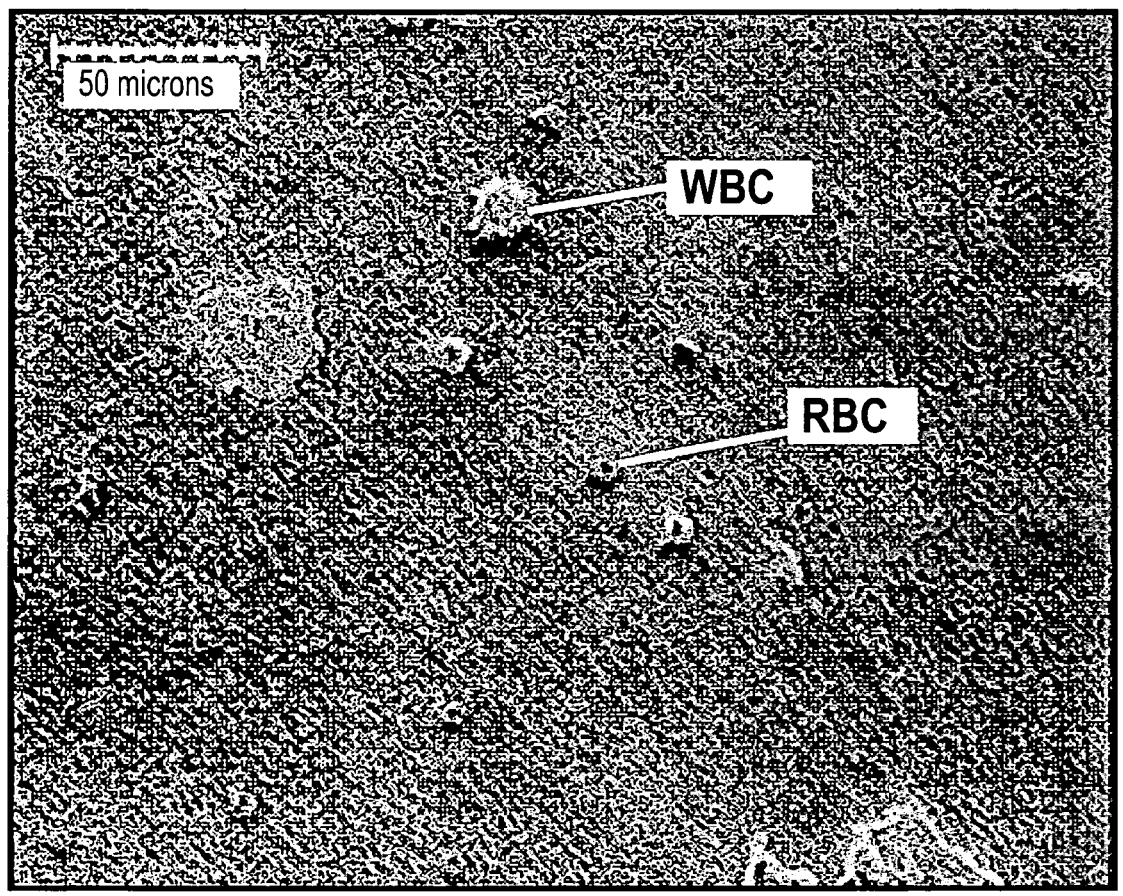
FIG. 11 is a duplicate of one of the figures described above (500×, chlorhexidine treated), where FIG. 11 indicates a white blood cell (WBC) and a red blood cell (RBC).

FIG. 11 is a duplicate of one of the figures described above (500×, chlorhexidine treated), where FIG. 11 indicates a white blood cell (WBC) and a red blood cell (RBC). The bar at the top left-hand side shows the length of 50 micrometers.

Figure 12:
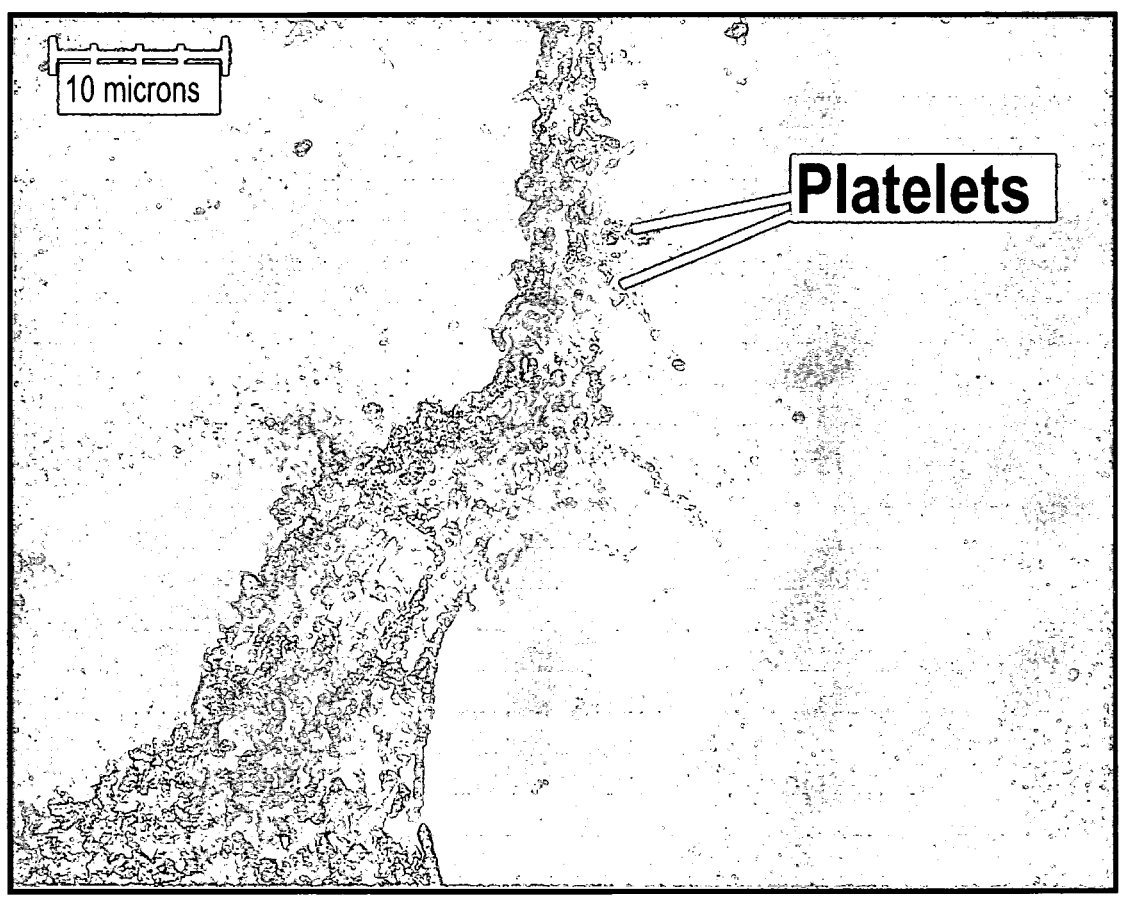
FIG. 12 is a duplicate of one of the figures described above (2000×, untreated) showing platelets.

FIG. 12 is a duplicate of one of the figures described above (2000×, untreated) showing platelets. The drawn lines indicate platelets. The bar at the top left-hand side shows the length of 10 micrometers.

EXAMPLES

Example 1

Solutions of varying alexidine concentrations (50-300 micrograms/mL) were incubated in individual test tubes, each containing 0.50 mL of human blood. The human blood was supplemented with 3.8% sodium citrate. The incubation was for 1 hour on a gyratory shaker set at 24 rpm and 37 degrees C. After 1 hour, 10 microliters of 500 Units/mL thrombin, and 60 microliters of 200 mM $CaCl_2$ was added to each of the incubating blood samples. Blood clotting time was then measured using a stop watch. Table 1 discloses the results. Alexidine samples showed longer thrombin clotting time or partial clotting in whole blood.

In a preferred, but non-limiting embodiment, the present disclosure provides medical device with a coating, impregnation, and combinations thereof, that comprises alexidine at 60 micrograms/cm$^2$, where this level of alexidine can induce equal or better anti-thrombogenic and anti-microbial responses than that of 300 micrograms/cm$^2$ chlorhexidine. The present disclosure provides treated medical devices, and related methods, where alexidine is at least as effective as chlorhexidine with 2-times to 5-times lesser concentrations than chlorhexidine on treated surfaces. A characteristic of the present disclosure, which uses alexidine, is that chlorhexidine at 60 micrograms/cm$^2$ is not effective for anti-blood clotting activity or for anti-microbial activity.

TABLE 1

| | Replicate 1 (min:sec) | Replicate 2 (min:sec) | Replicate 3 (min:sec) | Replicate 4 (min:sec) | Replicate 5 (min:sec) |
|---|---|---|---|---|---|
| Whole blood alone | 00:44 | 00:48 | 00:45 | 00:50 | 00:47 |
| Blood + 0.05 mg/mL alexidine | 02:02 | 02:00 | 02:10 | 02:05 | 02:15 |
| Blood + 0.1 mg/mL alexidine | 02:45 (loose clot) | 02:55 (loose clot) | 02:40 (loose clot) | 02:45 (loose clot) | 02:45 (loose clot) |
| Blood + 0.2 mg/mL alexidine | Greater than 72 hours (partial clotting) | | | | |
| Blood + 0.3 mg/mL alexidine | Greater than 72 hours (partial clotting) | | | | |

Thrombin clotting time in whole blood (minutes/seconds)

Example 2

Antimicrobial and anti-thrombogenic characteristics of peripherally inserted central catheters (PICCs) with alexidine were studied. Solutions containing 0.1-5% alexidine (wt./vol.), 2-10% Tecothane® (wt./vol.), and a solvent mixture of tetrahydrofuran (THF) and methanol are applicable for PICC treatment. A solution was prepared and applied to the external surface of 5.5 French (Fr), double lumen polyurethane PICCs treatment. The treated PICCs were dried in an oven set at 50 degrees C. for 0.5 hours, then room temperature for 24 hours, followed by sterilization with ethylene oxide. Subsequently, two-cm segments were cut from the sterilized catheters, and the amount of alexidine present per unit length was determined using HPLC. The length "5.5 Fr" refers to the distance across the tubular portion from outside diameter to the opposite outside diameter (it does not refer to the diameter distance that resides entirely in the lumen of the tubular portion).

Table 2 discloses the results. Table 2 shows alexidine content per unit length, as determined by HPLC.

TABLE 2

Alexidine content per unit length, or per unit surface area

| Sample | Alexidine (micrograms/cm) or (micrograms/square cm) | Average | Relative standard deviation (RSD) |
|---|---|---|---|
| 1 | 63.3 (133.0) | 63.7 (134.0) | 4.9 |
| 2 | 60.9 (127.9) | | |
| 3 | 67.1 (141.0) | | |

Catheter segments were analyzed for anti-thrombogenic activity using thrombin clotting time method, as described in Example 1. Segments (1 cm) from untreated or treated PICCs were incubated in individual test tubes, each containing 0.5 mL human blood (with 3.8% sodium citrate), for 1 hour at 37 degrees C. on a gyratory shaker set at 24 rpm. After 1 hour, segments from each incubating tube were removed, and aliquots of 0.430 mL blood were transferred to fresh tubes. Subsequently, 10 microliters of 500 Units/mL thrombin and 60 microliters of 200 mM $CaCl_2$ was added to each of the blood samples. Blood clotting time was then measured. Table 3 discloses the results. Alexidine samples showed longer thrombin clotting times in whole blood.

TABLE 3

Thrombin clotting time in whole blood (min:sec)

| | Replicate 1 (min:sec) | Replicate 2 (min:sec) | Replicate 3 (min:sec) | Replicate 4 (min:sec) | Replicate 5 (min:sec) |
|---|---|---|---|---|---|
| Whole blood alone | 00:44 | 00:48 | 00:45 | 00:50 | 00:47 |
| Untreated PICC | 00:41 | 00:36 | 00:38 | 00:38 | 00:38 |
| Alexidine PICC | 04:38 | 04:20 | 04:50 | 04:48 | 04:40 |

Antimicrobial activity of the alexidine treated PICC was evaluated against gram-positive and gram-negative bacteria, as well as fungi. For testing long term efficacy, segments from treated and untreated control PICCs were pro-soaked in human plasma for various time points between days 1 and 28, followed by challenge with $1.5 \times 10^5$ CFU/mL of *Staphylococcus aureus, Pseudomonas aeruginosa*, or *Candida albicans*, for 24 hours. "CFU" means, colony forming units. Organisms that adhered to segments were recovered by sonication, and quantified by plating and colony counting. Log 10 reduction was then calculated, and compared to the initial inoculum of the three organisms. Table 4 and FIG. 1 disclose the results. Alexidine samples showed greater than 5 log 10 reduction (99.999%) for up to 28 days for all the tested organisms.

Alexidine was incorporated into a polySB modified surface and evaluated for enhancing the anti-thrombogenic and antimicrobial activities. Polyurethane chronic hemodialysis catheters (CHDCs) and PICCs both modified with polySB, were treated with a solution containing 1.5% alexidine (wt./vol.) in a THF and methanol mixture. Treated catheters were then dried in an oven set at 35 degrees C., with drying for 24 hours, followed by sterilization with ethylene oxide. Segments of 1 cm length were obtained from sterile modified and unmodified (control) CHDCs and PICCs, and analyzed for anti-thrombogenic activity using thrombin clotting time method, as described above in Example 1. Table 5 discloses the blood clotting time results. Both PIC and CHDC samples with alexidine and polySB treatment showed partial clotting of whole blood. Thus, the polySB treatment did not have a negative influence on the anti-thrombogenic property of alexidine.

TABLE 4

Log10 reduction based on initial inoculum concentration

| | Log10 reduction | | | | |
|---|---|---|---|---|---|
| | Day 1 | Day 8 | Day 14 | Day 21 | Day 28 |
| *C. albicans* ATCC 10231 | | | | | |
| Treated PICC | 5.3 | 5.4 | 5.8 | 5.4 | 5.4 |
| Untreated PICC | 0.8 | 1.7 | 2.0 | 2.2 | 2.2 |
| Initial inoculum | 2.20e+05 | 2.60e+0.5 | 6.00e+0.5 | 2.40e+05 | 2.40e+05 |
| *S. aureus* ATCC 33591 | | | | | |
| Treated PICC | 5.2 | 5.2 | 5.2 | 5.2 | 5.2 |
| Untreated PICC | 0.4 | minus 0.8 | minus 1.6 | minus 0.6 | minus 0.6 |
| Initial inoculum | 1.50e+05 | 1.50e+0.5 | 1.50e+0.5 | 1.50e+05 | 1.50e+05 |
| *P. aeruginosa* ATCC 27853 | | | | | |
| Treated PICC | 5.2 | 5.2 | 5.2 | 5.2 | 5.2 |
| Untreated PICC | 1.9 | 1.4 | 1.0 | 1.6 | 1.3 |
| Initial inoculum | 1.50e+05 | 1.50e+0.5 | 1.50e+0.5 | 1.50e+05 | 1.50e+05 |

TABLE 5

Thrombin clotting time in whole blood (min:sec)

| | Replicate 1 (min:sec) | Replicate 2 (min:sec) | Replicate 3 (min:sec) | Replicate 4 (min:sec) | Replicate 5 (min:sec) |
|---|---|---|---|---|---|
| Untreated PICC | 00:41 | 00:36 | 00:38 | 00:38 | 00:38 |
| PICC treated with polySB plus alexidine | Over 72 hours (partial clotting) | | | | |
| Untreated CHDC | 00:52 | 00:58 | 00:58 | 00:52 | 00:55 |
| CHDC treated with polySB and alexidine | Over 72 hours (partial clotting) | | | | |

Example 3

Example 3 shows incorporation of alexidine in catheters modified with polymeric sulfobetaine (polySB). Vascular catheters with non-leaching polySB surface modification reduce platelet adhesion and microbial attachment through the coordination of water molecules to the catheter surface.

Example 4

The following provides a side-by-side comparison of alexidine with chlorhexidine. Fluid phase experiments were conducted to compare the influences of alexidine and chlorhexidine on thrombin clotting time (Table 6). Alexidine proved to be four times more potent than chlorhexidine in inhibiting blood clotting. The reaction mixtures contained freshly drawn human blood, alexidine or chlorhexidine as indicated, and exogenously added thrombin. The experiment was repeated five times, as indicated by replicates 1-5. The concentrations of alexidine or chlorhexidine that were used in the experiments were zero ug/mL (baseline), 3.125, 6.25, 12.5, 25, 50, or 100 ug/mL, as indicated. Baseline data demonstrated that clotting time without any added antimicrobial was rapid, that is, about 30 seconds. Where antimicrobials were used at a concentration of 6.25 ug/mL, clotting time in the presence of chlorhexidine was about thirty seconds and therefore was not detectably inhibited. In contrast, in the presence of alexidine (6.25 ug/mL), clotting time was about five minutes, and hence was markedly inhibited. This dramatic difference was also observed when higher concentrations of antimicrobials were used in the clotting reactions.

Hexamethyldisilazane for Scanning Electron Microscopy of Gastrotricha. Biotechnic & Histochemistry, 75: 41-44).

Step 5. Air dry in hood at room temperature, overnight (Slizova, D, Otakar, K, & Pospisilova, B. (2003) Alternative Method of Rapid Drying Vascular Specimans for Scanning Electron Microscopy. Journal of Endovascular Therapy, 10:285-187).

Step 6. Store for mounting.

Results from Scanning Electron Microscopy Analysis of Samples

As stated above, three types of samples were used: (1) Untreated samples, (2) Chlorhexidine treated samples, and (3) Alexidine treated samples. Following exposure of each of these samples to human blood, the samples were pro-

TABLE 6

| | | Thrombin Clotting Time in whole blood (min:sec) | | | | |
|---|---|---|---|---|---|---|
| | | Replicate 1 | Replicate 2 | Replicate 3 | Replicate 4 | Replicate 5 |
| Blood alone (baseline) | | 0:34 | 0:32 | 0:34 | 0:29 | 0:37 |
| Blood + Alexidine (µg/mL) | 100 | >24 hrs | >24 hrs | >24 hrs | >24 hrs | >24 hrs |
| | 50 | >24 hrs | >24 hrs | >24 hrs | >24 hrs | >24 hrs |
| | 25 | >24 hrs | >24 hrs | >24 hrs | >24 hrs | >24 hrs |
| | 12.5 | >24 hrs | >24 hrs | >24 hrs | >24 hrs | >24 hrs |
| | 6.25 | 5:00 | 4:49 | 5:00 | 6:33 | 4:25 |
| | 3.125 | 0:30 | 0:32 | 0:32 | 0:32 | 0:32 |
| Blood + Chlorhexidine (µg/mL) | 100 | >24 hrs | >24 hrs | >24 hrs | >24 hrs | >24 hrs |
| | 50 | >24 hrs | >24 hrs | >24 hrs | >24 hrs | >24 hrs |
| | 25 | 4:55 | 5:00 | 5:00 | 5:00 | 5:00 |
| | 12.5 | 0:31 | 0:30 | 0:29 | 0:32 | 0:31 |
| | 6.25 | 0:30 | 0:32 | 0:30 | 0:30 | 0:33 |
| | 3.125 | 0:30 | 0:33 | 0:29 | 0:32 | 0:32 |

Example 5

Treating Catheter Segments with Human Blood, Prior to Preparing for Scanning Electron Microscopy Each test article (1 cm segments) was incubated for 1 hour in whole human blood containing 3.8% sodium citrate on an incubator shaker set at 75 rpm and 37° C. After this 1 hour blood exposure, samples were rinsed in PBS 3 times, and then fixed and processed for SEM.

Example 6

Sample Preparation for Scanning Electron Microscopy

The following non-limiting procedure was used for preparing samples for scanning electron microscopy (SEM). Without implying any limitation on the samples, or on the reagents and methods, the procedure involved the following steps.

Step 1. Rinse with Phosphate Buffered Saline (PBS) to remove weakly bound cells.

Step 2. Fix in 2.5% glutaraldehyde solution (made in PBS) for 30 min at room temperature (Vijayanand, K, Pattanayak, D, Mohan, T, & Banerjee, R. (2005) Interpreting Blood-Biomaterial Interactions from Surface Free Energy and Work of Adhesion. Trends in Biomaterials and Artificial Organs 18:73-83).

Step 3. Dry in an ethanol series in water (60, 70, 80, 90, 100%) 5 min each (Vijayanand, supra).

Step 4. Immerse in 100% Hexamethyldisilazane for 15 minutes, 2× each (Hochberg, R & Litvaitis, M. (2000)

cessed and then examined by scanning electron microscopy (SEM). SEM analysis revealed the relative density of blood cells adhering to the samples. As detailed above, the blood cells that were visible under SEM included white blood cells (WBCs), red blood cells (RBCS), and platelets. As is most evident from the 500-fold magnification pictures and from the 2000-fold magnification pictures, the untreated samples contained the greatest density of adhering blood cells. The SEM data also demonstrates that the chlorhexidine-treated samples contained lesser densities of cells, and that the alexidine-treated samples contained the lowest densities of cells.

The present disclosure provides alexidine-treated samples that are capable of supporting cell adhesion at a density that is less than 90% that of a corresponding chlorhexidine-coated sample, less than 85%, less than 80%, less than 75%, less than 70%, less than 65% less than 60%, less than 55%, less than 50%, less than 45%, less than 40%, less than 35%, less than 30%, less than 25%, less than 20%, less than 15%, less than 10%, or less than 5%, of a corresponding chlorhexidine-treated sample.

The present disclosure provides alexidine-coated samples that are capable of supporting cell adhesion at a density that is less than 90% that of a corresponding chlorhexidine-coated sample, less than 85%, less than 80%, less than 75%, less than 70%, less than 65% less than 60%, less than 55%, less than 50%, less than 45%, less than 40%, less than 35%, less than 30%, less than 25%, less than 20%, less than 15%, less than 10%, or less than 5%, of a corresponding chlorhexidine-coated sample.

Also, the present disclosure provides alexidine-impregnated samples that are capable of supporting cell adhesion at a density that is less than 90% that of a corresponding chlorhexidine-impregnated sample, less than 85%, less than 80%, less than 75%, less than 70%, less than 65% less than 60%, less than 55%, less than 50%, less than 45%, less than 40%, less than 35%, less than 30%, less than 25%, less than 20%, less than 15%, less than 10%, or less than 5%, of a corresponding chlorhexidine-impregnated sample.

Also, the present disclosure provides alexidine-soaked (or dipped) samples that are capable of supporting cell adhesion at a density that is less than 90% that of a corresponding chlorhexidine-soaked (or dipped) sample, less than 85%, less than 80%, less than 75%, less than 70%, less than 65% less than 60%, less than 55%, less than 50%, less than 45%, less than 40%, less than 35%, less than 30%, less than 25%, less than 20%, less than 15%, less than 10%, or less than 5%, of a corresponding chlorhexidine-soaked (or dipped) sample.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A medical device adapted for contact with a vessel or cavity in the body, the medical device including a tubular portion, comprising:
    an external coating or impregnation comprising alexidine in an amount that is 200 µg/cm$^2$ to 300 µg/cm$^2$; and
    an internal coating or impregnation comprising alexidine in an amount that is less concentrated than the external coating or impregnation.

2. The medical device of claim 1, wherein at least one of the external and internal coatings or impregnations further comprise a non-alexidine solute.

3. The medical device of claim 2, further comprising:
    an external substance solute group composed of all solutes present in the external coating or impregnation, wherein the external substance solute group includes at least one non-alexidine solute, and
    an internal substance solute group composed of all solutes present in the internal coating or impregnation, wherein the internal substance solute group includes at least one non-alexidine solute, wherein
    (i) the external substance solute group is not the same as the internal substance solute group or
    (ii) at least one solute is at a different concentration in the external substance solute group than in the internal substance solute group.

4. The medical device of claim 3, further comprising at least one distinguishing solute present in only one of the external substance solute group or the internal substance solute group, wherein (i) the at least one distinguishing solute comprises a polymer that is not covalently bound to the medical device, or (ii) the at least one distinguishing solute comprises an anion.

5. The medical device of claim 4, wherein the at least one distinguishing solute comprises: (i) a polyurethane polymer that is not covalently bound to the medical device, or (ii) an ion that is acetate ion or gluconate ion.

6. The medical device of claim 1, wherein the alexidine is capable of (i) reducing a thrombogenic event that takes place on at least one of the external surface and the internal surface, and (ii) reducing microbial activity that takes place on at least one of the external surface and the internal surface.

7. The medical device of claim 1, wherein the external coating or impregnation comprises alexidine at a concentration capable of reducing thrombogenic events, whereby a comparator medical device having an external coating or impregnation comprising chlorohexidine at the same concentration as alexidine is not capable of detectably reducing thrombogenic events.

8. The medical device of claim 1, wherein the external coating or impregnation comprises alexidine at a concentration that is capable of reducing thrombogenic events to a range of 0-50%, relative to an uninhibited thrombogenic event level defined as 100% whereby a comparator medical device having an external coating or impregnation comprising chlorhexidine at the same concentration is capable of reducing thrombogenic events to a range of 90.0-99.9%, relative to the uninhibited thrombogenic event level is defined as 100%.

9. The medical device of claim 1, wherein the internal coating or impregnation comprises alexidine at a concentration that is capable of reducing thrombogenic events to a relatively large extent that is in the range of 0-50%, relative to an uninhibited thrombogenic event level defined as 100%, whereby a comparator medical device having an internal coating or impregnation comprising chlorhexidine at the same said concentration is capable of reducing thrombogenic events to a range of 90.0-99.9%, where the uninhibited thrombogenic event level is defined as 100%.

10. The medical device of claim 1, wherein the medical device comprises at least one of the group consisting of: alexidine, alexidine hydrochloride, alexidine dihydrochloride, alexidine monoacetate, alexidine diacetate, alexidine gluconate, or alexidine digluconate.

11. The medical device of claim 2, wherein the external coating or impregnation includes the same non-alexidine solutes as the internal coating or impregnation.

12. The medical device of claim 1, wherein the concentration of alexidine is sufficient to result in a change in blood clotting time of at least 150% or at least a 50% increase in blood clotting time, as compared to blood clotting time of a control medical device that does not comprise alexidine measured using human whole blood.

13. The medical device of claim 1, wherein the concentration of alexidine is sufficient to result in less than 90% of maximal platelet deposition on the medical device, as compared to platelet deposition with a control medical device that does not comprise alexidine, wherein maximal platelet deposition is defined as 100%.

14. The medical device of claim 1, wherein the alexidine is bulk distributed.

15. The medical device of claim 1, wherein the medical device comprises one or more of a catheter, cannula, elongated tube, valve, or implant port.

16. The medical device of claim 1, wherein the medical device is adapted for contact with or insertion into at least one of the vascular system, the urinary tract, or the respiratory system.

17. The medical device of claim 1, further comprising a coating comprising polyether polyurethane, polyester polyurethane, polycarbonate polyurethane, or polydimethylsiloxane polyurethane.

18. The medical device of claim 1, wherein at least one of the external and internal coatings or impregnations further comprises (i) polysulfobetaine, (ii) polycarboxybetaine, or (iii) polysulfobetaine and polycarboxybetaine.

19. The medical device of claim 1, wherein at least one of the external and internal coatings or impregnations further comprises a co-polymer of silicone macrodiols and polyurethanes.

20. The medical device of claim 1, wherein one of the external coating and the internal coating has a thickness ranging from 1 nanometer to 1 millimeter.

21. The medical device of claim 1, wherein one of the external impregnation and the internal impregnation extends 1 nanometer to 1 millimeter from the surface of the medical device into the medical device.

22. The medical device of claim 1, wherein the concentration of alexidine in the internal coating compared to the external coating differs by at least 1.25-fold.

23. The medical device of claim 1, wherein the external and the internal coatings or impregnations do not include an anti-microbial agent or an anti-thrombogenic agent that is not alexidine.

* * * * *